(12) United States Patent
Wasserscheid et al.

(10) Patent No.: US 8,642,778 B2
(45) Date of Patent: Feb. 4, 2014

(54) IONIC LIQUIDS

(75) Inventors: Peter Wasserscheid, Erlangen (DE); Natalia Paape, Wiesbaden (DE); Andreas Boesmann, Hessdorf (DE); Peter Schulz, Erlangen (DE)

(73) Assignee: Merck Patent GmbH, Darmstadt (DE)

( * ) Notice: Subject to any disclaimer, the term of this patent is extended or adjusted under 35 U.S.C. 154(b) by 371 days.

(21) Appl. No.: 12/994,323

(22) PCT Filed: May 12, 2009

(86) PCT No.: PCT/EP2009/003373
§ 371 (c)(1),
(2), (4) Date: Feb. 23, 2011

(87) PCT Pub. No.: WO2009/152902
PCT Pub. Date: Dec. 23, 2009

(65) Prior Publication Data
US 2011/0152537 A1    Jun. 23, 2011

(30) Foreign Application Priority Data
May 28, 2008 (EP) .................................... 08009697

(51) Int. Cl.
C07D 233/20 (2006.01)
C07D 233/64 (2006.01)
C07D 251/10 (2006.01)
C07D 327/04 (2006.01)
C07D 327/06 (2006.01)

(52) U.S. Cl.
USPC ................ 548/316.4; 549/9; 549/13; 549/29; 549/30

(58) Field of Classification Search
USPC ........... 548/316.4; 514/396; 549/9, 13, 29, 30
See application file for complete search history.

(56) References Cited

PUBLICATIONS

Cole, A. C. et al., "Novel bronsted acidic ionic liquids and their use as dual solvent—catalysts," Journal of the American Chemical Society, 2002, vol. 124, pp. 5962-5963.*
Etienne, A. et al, C.R. Acad. Sci. Paris (1970), pp. 841-844.*
Abstract of Polonka et al (2005), XP 002569034.*
Abstract of Ozaki et al (1993), XP 002569037.*
Abstract of Ram et al (1995), XP 002569036.*
Cole et al, J. Am. Chem. Society, 2002, vol. 124, pp. 5962-5963.*

Dalvi-Malhotra, J. et al., "Enhanced Conjugated Polymer Fluorescence Quenching by Dipyridinium-based quenchers in the presence of surfactant," J. Phys. Chem., 2005, vol. 109, pp. 3873-3878.
Etienne, A. et al., "Sur la preparation des esters d'acides sulfoniques," C. R. Acad. Sc., Mar. 2, 1970, pp. 841-844.
Gao, F. et al., "Synthesis and use of sulfonamide-, sulfoxide-, or sulfone-containing aminoglycoside-CoA bisubstrates as mechanistic probes for aminoglycoside N-6'-acetyltransferase," Bioorganic and Medicinal Chemistry Letters, 2008, vol. 18, pp. 5518-5522.
Gaylord, B. S. et al., "Water-soluble conjugated oligomers: effect of chain length and aggregation on photoluminescence—quenching efficiencies," Journal of the American Chemistry Society, 2001, vol. 123, pp. 6417-6418.
Iwamoto, T., "Manufacture of emulsified compositions containing polysilicones and water-swelling clay minerals and detergent compositions containing the amulsions," 2001, XP002569035.
Jodaikin, A. et al., "Reshapable retention device for fixation at a dental site," 2009, XP002569041.
Lauer, W. M. et al., "The Addition of Sodium Bisulfite to Alkylene Oxides," Contribution from the School of Chemistry of the University of Minnesota, Oct. 1936, vol. 58, pp. 1873-1874.
Nanasawa, M. et al., "Synthesis of Novel 4,4'-benzidine derivatives with sulfonic acid groups," OPPI Briefs, 2006, vol. 38, No. 3, pp. 341-344.
Ozaki, T. et al., "Epoxy resin (meth)acrylates, their manufacture, and polymerizable compositions containing them," 1994, XP002569037.
Polonka, J. et al., "Beauty wash product compositions with solid particulate optical modifiers, such as titanium dioxide, delivering enhanced visual benefits to the skin," 2005, XP002569034.
Ram, M. S. et al., "Syntheses, Reactivity, and Molecular Structures of RSRS-[Ni(tmc)SC$_6$H$_5$](PF$_6$), RRSS-[Ni(tmc)SC$_6$H$_5$](CF$_3$SO$_3$), and RRSS-[Ni(tmc)](CF$_3$SO$_3$) (tmc= 1,4,8,11-Tetramethyl-1, 4,8,11-tetraazacyclotetradecane)," Inorg. Chem, 1995, vol. 34, pp. 5884-5892.
Ram, M. S. et al., "Syntheses, Reactivity, and Molecular Structures of RSRS-[Ni(tmc)SC$_6$H$_5$](PF$_6$), RRSS-[Ni(tmc)SC$_6$H$_5$](CF$_3$SO$_3$), and RRSS-[Ni(tmc)](CF$_3$SO$_3$) (tmc= 1,4,8,11-Tetramethyl-1,4,8,11-tetraazacyclotetradecane)," 1995, XP002569036.
Shi, W. et al., "Synthesis of novel triphenylamine-based conjugated polyelectrolytes and their application as hole-transport layers in polymeric light-emitting diodes," Journal of Materials Chemistry, 2006, vol. 16, pp. 2387-2394.
Willems, J. et al., "The aliphatic hydroxysulphonic acids and their internal esters: The sultones—Part 2. The Sultones," Bull. Soc. Chim. Belg., 1955, vol. 64, pp. 747-771.

* cited by examiner

*Primary Examiner* — Kamal Saeed
*Assistant Examiner* — Janet L Coppins
(74) *Attorney, Agent, or Firm* — Millen, White, Zelano & Branigan, P.C.

(57) ABSTRACT

The present invention relates to chemical compounds comprising a $[Y(CHR^a)_n—CH(R^a)SO_3]^-$ anion, their preparation and application. The chemical compounds are preferably ionic liquids.

19 Claims, 2 Drawing Sheets

IONIC LIQUIDS

Figure 1:
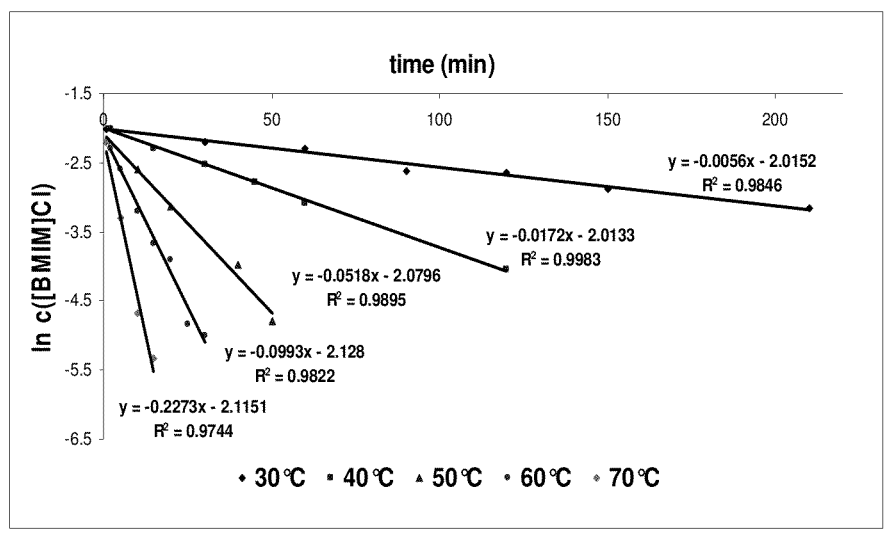

The present invention relates to chemical compounds comprising a $[Y(CHR^a)_n\text{—}CH(R^a)SO_3]^-$ anion, their preparation and application. The chemical compounds are preferably ionic liquids.

Ionic liquids or liquid salts are typically ionic species which consist of an organic cation and a generally inorganic anion. They preferably do not comprise neutral molecules and usually have melting points below 373 K. In the context of this patent application the term "ionic liquid" is used as a synonym to chemical compound or compound.

Intensive research is currently being carried out in the area of ionic liquids since the potential applications are multifarious. Review articles on ionic liquids are, for example, R. Sheldon "Catalytic reactions in ionic liquids", *Chem. Commun.*, 2001, 2399-2407; M. J. Earle, K. R. Seddon "Ionic liquids. Green solvent for the future", *Pure Appl. Chem.*, 72 (2000), 1391-1398; P. Wasserscheid, W. Keim "Ionic Flüssigkeiten—neue Lösungen für die Übergangsmetallkatalyse" [Ionic Liquids—Novel Solutions for Transition-Metal Catalysis], *Angew. Chem.*, 112 (2000), 3926-3945; T. Welton "Room temperature ionic liquids. Solvents for synthesis and catalysis", *Chem. Rev.*, 92 (1999), 2071-2083 or R. Hagiwara, Ya. Ito "Room temperature ionic liquids of alkylimidazolium cations and fluoroanions", *J. Fluorine Chem.*, 105 (2000), 221-227.

The properties of ionic liquids, for example melting point, thermal and electrochemical stability and viscosity, are greatly influenced by the nature of the anion. By contrast, the polarity and hydrophilicity or lipophilicity can be varied through a suitable choice of the cation/anion pair.

There is always a demand for new and improved compounds suitable as ionic liquids and processes for the production of such compounds.

A first object of the present invention therefore is a process according to claim 1.

A second object are compounds obtainable via this process, as described in claims 4 to 10.

A third object of the present invention is the use of these compounds or of compounds obtainable by the described process as ionic liquid or in a typical ionic liquid application, as described in detail below.

There are no restrictions per se with respect to the choice $Kt^+$ of the cation of the chemical compounds in accordance with the present invention. However, preference is given to non-metallic cations, e.g. to organic cations particularly preferably ammonium, phosphonium, uronium, thiouronium, guanidinium or heterocyclic cations. Suitable metallic cations for use in the process described in the claims or the description below are $K^+$, $Na^+$, $Cs^+$ or $Rb^+$.

Ammonium cations can be described, for example, by the formula (1)

where

R in each case, independently of one another, denotes

H, with the proviso that at least two substituents R in the formula (1) are H, OR', $NR'_2$, with the proviso that at most one substituent R in the formula (1) is OR' or $NR'_2$, straight-chain or branched alkyl having 1-20 C atoms, straight-chain or branched alkenyl having 2-20 C atoms and one or more double bonds, straight-chain or branched alkynyl having 2-20 C atoms and one or more triple bonds, saturated, partially or fully unsaturated cycloalkyl having 3-7 C atoms, which may be substituted by alkyl groups having 1-6 C atoms, where one or more R may be partially or fully substituted by halogens, in particular —F and/or —Cl, or partially by —OH, —OR', —CN, —C(O)OH, —C(O)NR'$_2$, —SO$_2$NR'$_2$, —C(O)X', —SO$_2$OH, —SO$_2$X' or —NO$_2$, and where one or two non-adjacent carbon atoms of the R which are not in the α-position may be replaced by atoms and/or atom groups selected from the group —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— and —P(O)R'—, where R' may be =H, non-, partially or perfluorinated $C_1$- to $C_6$-alkyl, $C_3$- to $C_7$-cycloalkyl, or unsubstituted or substituted phenyl, and X' may be halogen.

Phosphonium cations can be described, for example, by the formula (2)

where $R^2$ in each case, independently of one another, denotes H, OR', NR'$_2$, straight-chain or branched alkyl having 1-20 C atoms, straight-chain or branched alkenyl having 2-20 C atoms and one or more double bonds, straight-chain or branched alkynyl having 2-20 C atoms and one or more triple bonds, saturated, partially or fully unsaturated cycloalkyl having 3-7 C atoms, which may be substituted by alkyl groups having 1-6 C atoms, where one or more $R^2$ may be partially or fully substituted by halogens, in particular —F and/or —Cl, or partially by —OH, —OR', —CN, —C(O)OH, —C(O)NR'$_2$, —SO$_2$NR'$_2$, —C(O)X', —SO$_2$OH, —SO$_2$X' or —NO$_2$, and where one or two non-adjacent carbon atoms of the $R^2$ which are not in the α-position may be replaced by atoms and/or atom groups selected from the group —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— and —P(O)R'—, where R'=H, non-, partially or perfluorinated $C_1$- to $C_6$-alkyl, $C_3$- to $C_7$-cycloalkyl, or unsubstituted or substituted phenyl, and X'=halogen.

However, cations of the formulae (1) and (2) in which all four or three substituents R and $R^2$ are fully substituted by halogens are excluded, for example the tris(trifluoromethyl)methylammonium cation, the tetra(trifluoromethyl)ammonium cation or the tetra(nonafluorobutyl)ammonium cation.

Uronium cations can be described, for example, by the formula (3)

and thiouronium cations can be described by the formula (4)

where $R^3$ to $R^7$ each, independently of one another, denote hydrogen, where hydrogen is excluded for $R^5$, straight-chain or branched alkyl having 1 to 20 C atoms, straight-chain or branched alkenyl having 2-20 C atoms and one or more double bonds, straight-chain or branched alkynyl having 2-20 C atoms and one or more triple bonds, saturated, partially or fully unsaturated cycloalkyl having 3-7 C atoms, which may be substituted by alkyl groups having 1-6 C atoms, where one or more of the substituents $R^3$ to $R^7$ may be partially or fully substituted by halogens, in particular —F and/or —Cl, or partially by —OH, —OR', —CN, —C(O)OH, —C(O)NR'$_2$, —SO$_2$NR'$_2$, —C(O)X', —SO$_2$OH, —SO$_2$X' or —NO$_2$, and where one or two non-adjacent carbon atoms of $R^3$ to $R^7$ which are not in the α-position may be replaced by atoms and/or atom groups selected from the group —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— and —P(O)R'—, where R'=H, non-, partially or perfluorinated C$_1$- to C$_6$-alkyl, C$_3$- to C$_7$-cycloalkyl, or unsubstituted or substituted phenyl, and X'=halogen.

Guanidinium cations can be described by the formula (5)

$$[C(NR^8R^9)(NR^{10}R^{11})(NR^{12}R^{13})]^+ \qquad (5),$$

where
$R^8$ to $R^{13}$ each, independently of one another, denote hydrogen, —CN, NR'$_2$, —OR',
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms,
which may be substituted by alkyl groups having 1-6 C atoms, where one or more of the substituents $R^8$ to $R^{13}$ may be partially or fully substituted by halogens, in particular —F and/or —Cl, or partially by —OH, —OR', —CN, —C(O)OH, —C(O)NR'$_2$, —SO$_2$NR'$_2$, —C(O)X', —SO$_2$OH, —SO$_2$X' or —NO$_2$, and where one or two non-adjacent carbon atoms of $R^8$ to $R^{13}$ which are not in the α-position may be replaced by atoms and/or atom groups selected from the group —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— and —P(O)R'—, where R'=H, non-, partially or perfluorinated C$_1$- to C$_6$-alkyl, C$_3$- to C$_7$-cycloalkyl, or unsubstituted or substituted phenyl, and X'=halogen.

In addition, it is possible to employ cations of the general formula (6)

$$[HetN]^+ \qquad (6)$$

where
HetN$^+$ denotes a heterocyclic cation selected from the group

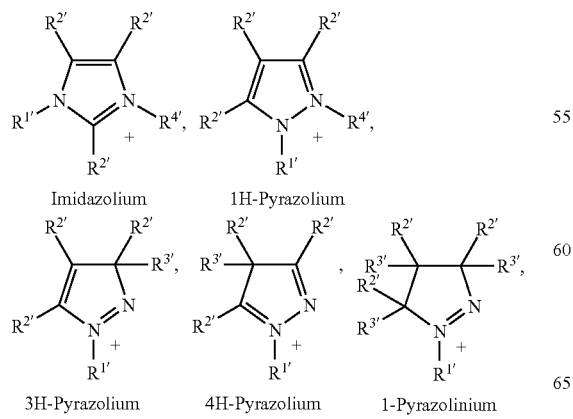
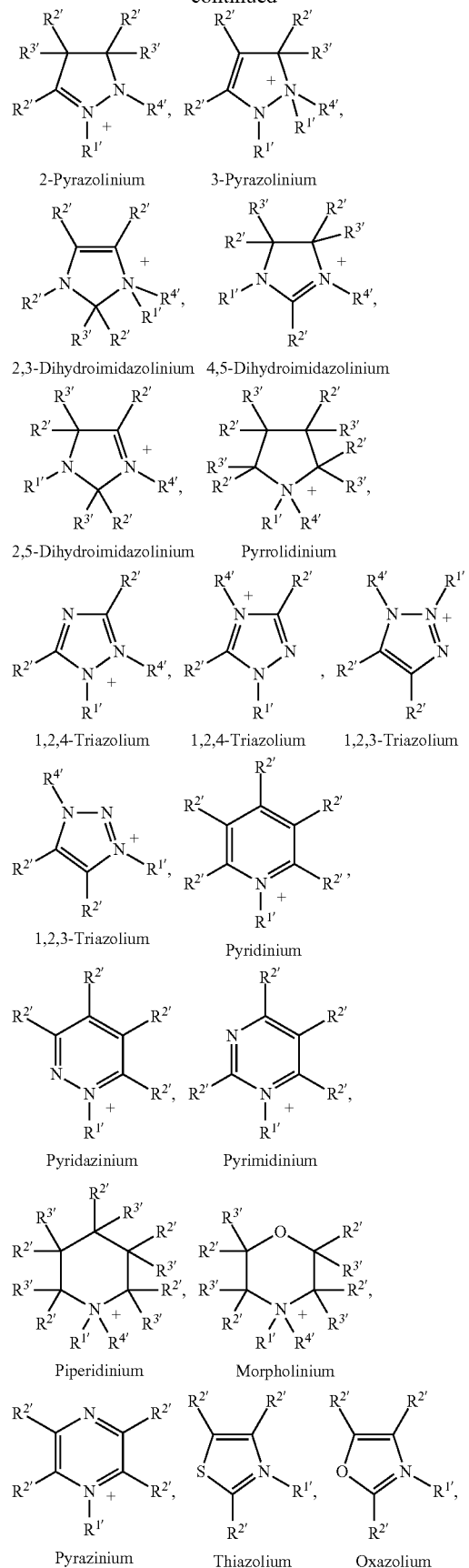

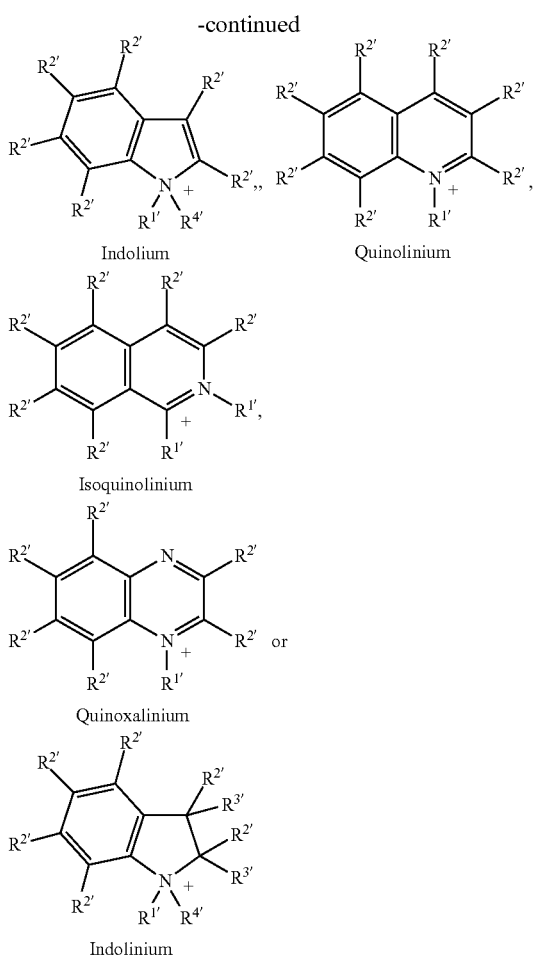

Indolium

Quinolinium

Isoquinolinium

Quinoxalinium

Indolinium where the substituents $R^{1'}$ to $R^{4'}$ each, independently of one another, denote hydrogen, —CN, —OR', —NR'$_2$, —P(O)R'$_2$, —P(O)(OR')$_2$, —P(O)(NR'$_2$)$_2$, —C(O)R', —C(O)OR', straight-chain or branched alkyl having 1-20 C atoms, straight-chain or branched alkenyl having 2-20 C atoms and one or more double bonds, straight-chain or branched alkynyl having 2-20 C atoms and one or more triple bonds, saturated, partially or fully unsaturated cycloalkyl having 3-7 C atoms, which may be substituted by alkyl groups having 1-6 C atoms, saturated, partially or fully unsaturated heteroaryl, heteroaryl-$C_1$-$C_6$-alkyl or aryl-$C_1$-$C_6$-alkyl, where the substituents $R^{1'}$, $R^{2'}$, $R^{3'}$ and/or $R^{4'}$ together may also form a ring system, where one or more substituents $R^{1'}$ to $R^{4'}$ may be partially or fully substituted by halogens, in particular —F and/or —Cl, or —OH, —OR', —CN, —C(O)OH, —C(O)NR'$_2$, —SO$_2$NR'$_2$, —C(O)X', —SO$_2$OH, —SO$_2$X' or —NO$_2$, but where $R^{1'}$ and $R^{4'}$ cannot simultaneously be fully substituted by halogens, and where one or two non-adjacent carbon atoms of the substituents $R^{1'}$ to $R^{4'}$ which are not bonded to the heteroatom may be replaced by atoms and/or atom groups selected from —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— and —P(O)R'—, where R'=H, non-, partially or perfluorinated $C_1$- to $C_6$-alkyl, $C_3$- to $C_7$-cycloalkyl, or unsubstituted or substituted phenyl, and X'=halogen.

For the purposes of the present invention, fully unsaturated substituents are also taken to mean aromatic substituents.

In accordance with the invention, suitable substituents R and $R^2$ to $R^{13}$ of the compounds of the formulae (1) to (5), besides hydrogen, are preferably: $C_1$- to $C_{20}$-, in particular $C_1$- to $C_{14}$-alkyl groups, and saturated or unsaturated, i.e. also aromatic, $C_3$- to $C_7$-cycloalkyl groups, which may be substituted by $C_1$- to $C_6$-alkyl groups, in particular phenyl.

The substituents R and $R^2$ in the compounds of the formula (1) or (2) may be identical or different. The substituents R and $R^2$ are preferably different.

The substituents R and $R^2$ are particularly preferably methyl, ethyl, iso-propyl, propyl, butyl, sec-butyl, tert-butyl, pentyl, hexyl, octyl, decyl or tetra-decyl.

Up to four substituents of the guanidinium cation $[C(NR^8R^9)(NR^{10}R^{11})(NR^{12}R^{13})]^+$ may also be bonded in pairs in such a way that mono-, bi- or polycyclic cations are formed.

Without restricting generality, examples of such guanidinium cations are:

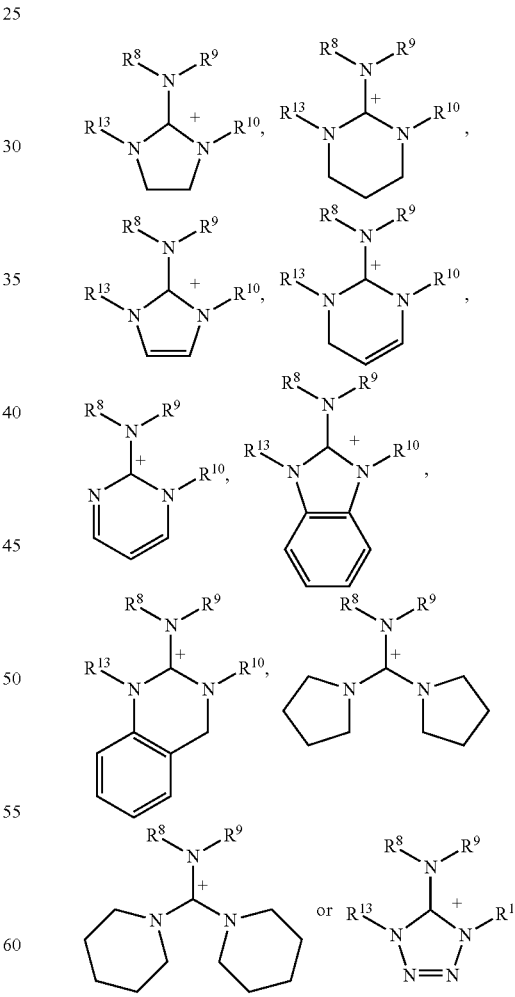

where the substituents $R^8$ to $R^{10}$ and $R^{13}$ can have a meaning or particularly preferred meaning indicated above.

If desired, the carbocyclic or heterocyclic rings of the guanidinium cations indicated above may also be substituted by $C_1$- to $C_6$-alkyl, $C_1$- to $C_6$-alkenyl, $NO_2$, F, Cl, Br, I, OH, $C_1$-$C_6$-alkoxy, $SCF_3$, $SO_2CF_3$, COOH, $SO_2NR'_2$, $SO_2X'$ or $SO_3H$, where X' and R' have a meaning indicated above, substituted or unsubstituted phenyl or an unsubstituted or substituted heterocycle.

Up to four substituents of the uronium cation $[C(R^3R^4N)(OR^5)(NR^6R^7)]^+$ or thiouronium cation $[C(R^3R^4N)(SR^5)(NR^6R^7)]^+$ may also be bonded in pairs in such a way that mono-, bi- or polycyclic cations are formed.

Without restricting generality, examples of such cations are indicated below, where Y=O or S:

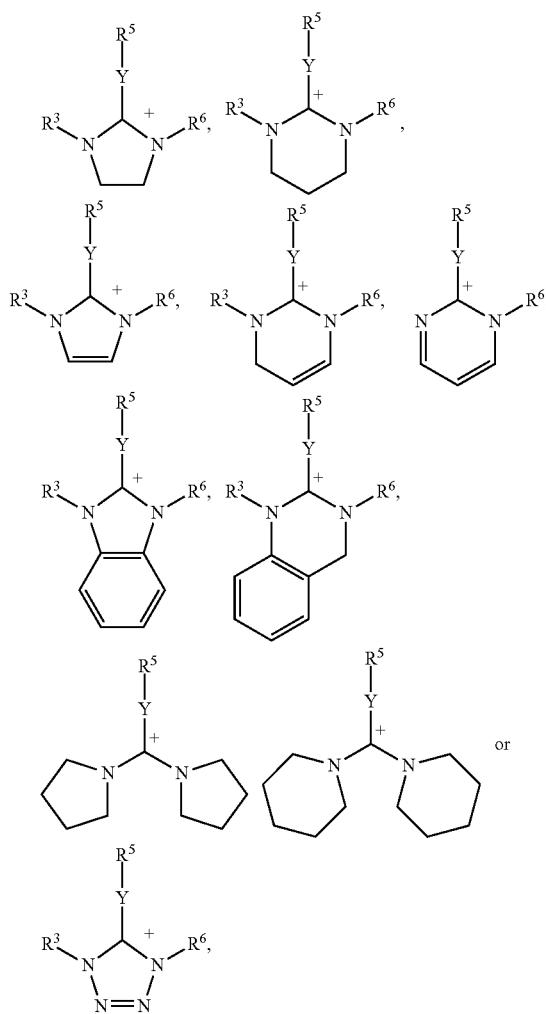

where the substituents $R^3$, $R^5$ and $R^6$ can have a meaning or particularly preferred meaning indicated above.

If desired, the carbocyclic or heterocyclic rings of the cations indicated above may also be substituted by $C_1$- to $C_6$-alkyl, $C_1$- to $C_6$-alkenyl, $NO_2$, F, Cl, Br, I, OH, $C_1$-$C_6$-alkoxy, $SCF_3$, $SO_2CF_3$, COOH, $SO_2NR'_2$, $SO_2X'$ or $SO_3H$ or substituted or unsubstituted phenyl or an unsubstituted or substituted heterocycle, where X' and R' have a meaning indicated above. The substituents $R^3$ to $R^{13}$ are each, independently of one another, preferably a straight-chain or branched alkyl group having 1 to 10 C atoms. The substituents $R^3$ and $R^4$, $R^6$ and $R^7$, $R^8$ and $R^9$, $R^{10}$ and $R^{11}$, $R^{12}$ and $R^{13}$ in compounds of the formulae (3) to (5) may be identical or different here. $R^3$ to $R^{13}$ are particularly preferably each, independently of one another, methyl, ethyl, n-propyl, isopropyl, n-butyl, tert-butyl, sec-butyl, phenyl or cyclohexyl, very particularly preferably methyl, ethyl, n-propyl, isopropyl or n-butyl.

In accordance with the invention, suitable substituents $R^{1'}$ $R^{4'}$ of compounds of the formula (6), besides hydrogen, are preferably: $C_1$- to $C_{20}$-, in particular $C_1$- to $C_{12}$-alkyl groups, and saturated or unsaturated, i.e. also aromatic, $C_3$- to $C_7$-cycloalkyl groups, which may be substituted by $C_1$- to $C_6$-alkyl groups, in particular phenyl.

The substituents $R^{1'}$ and $R^{4'}$ are each, independently of one another, particularly preferably methyl, ethyl, isopropyl, propyl, butyl, sec-butyl, tert-butyl, pentyl, hexyl, octyl, decyl, cyclohexyl, phenyl or benzyl. They are very particularly preferably methyl, ethyl, n-butyl or hexyl. In pyrrolidinium, piperidinium or indolinium compounds, the two substituents $R^{1'}$ and $R^{4'}$ are preferably different.

The substituent $R^{2'}$ or $R^{3'}$ is in each case, independently of one another, in particular hydrogen, methyl, ethyl, isopropyl, propyl, butyl, sec-butyl, tert-butyl, cyclohexyl, phenyl or benzyl. $R^{2'}$ is particularly preferably hydrogen, methyl, ethyl, isopropyl, propyl, butyl or sec-butyl. $R^{2'}$ and $R^{3'}$ are very particularly preferably hydrogen.

The $C_1$-$C_{12}$-alkyl group is, for example, methyl, ethyl, isopropyl, propyl, butyl, sec-butyl or tert-butyl, furthermore also pentyl, 1-, 2- or 3-methylbutyl, 1,1-, 1,2- or 2,2-dimethylpropyl, 1-ethylpropyl, hexyl, heptyl, octyl, nonyl, decyl, undecyl or dodecyl, optionally difluoromethyl, trifluoromethyl, pentafluoroethyl, heptafluoropropyl or nonafluorobutyl.

A straight-chain or branched alkenyl having 2 to 20 C atoms, in which a plurality of double bonds may also be present, is, for example, allyl, 2- or 3-butenyl, isobutenyl, sec-butenyl, furthermore 4-pentenyl, isopentenyl, hexenyl, heptenyl, octenyl, —$C_9H_{17}$, —$C_{10}H_{19}$ to —$C_{20}H_{39}$, preferably allyl, 2- or 3-butenyl, isobutenyl, sec-butenyl, furthermore preferably 4-pentenyl, isopentenyl or hexenyl.

A straight-chain or branched alkynyl having 2 to 20 C atoms, in which a plurality of triple bonds may also be present, is, for example, ethynyl, 1- or 2-propynyl, 2- or 3-butynyl, furthermore 4-pentynyl, 3-pentynyl, hexynyl, heptynyl, octynyl, —$C_9H_{15}$, —$C_{10}H_{17}$ to —$C_{20}H_{37}$, preferably ethynyl, 1- or 2-propynyl, 2- or 3-butynyl, 4-pentynyl, 3-pentynyl or hexynyl.

Aryl-$C_1$-$C_6$-alkyl denotes, for example, benzyl, phenylethyl, phenylpropyl, phenylbutyl, phenylpentyl or phenylhexyl, where both the phenyl ring and also the alkylene chain may be partially or fully substituted, as described above, by halogens, in particular —F and/or —Cl, or partially by —OH, —OR', —CN, —C(O)OH, —C(O)NR'$_2$, —SO$_2$NR'$_2$, —C(O)X, —SO$_2$OH, —SO$_2$X, —NO$_2$.

Unsubstituted saturated or partially or fully unsaturated cycloalkyl groups having 3-7 C atoms are therefore cyclopropyl, cyclobutyl, cyclopentyl, cyclohexyl, cycloheptyl, cyclopentenyl, cyclopenta-1,3-dienyl, cyclohexenyl, cyclohexa-1,3-dienyl, cyclohexa-1,4-dienyl, phenyl, cycloheptenyl, cyclohepta-1,3-dienyl, cyclohepta-1,4-dienyl or cyclohepta-1,5-dienyl, each of which may be substituted by $C_1$- to $C_6$-alkyl groups, where the cycloalkyl group or the cycloalkyl group substituted by $C_1$- to $C_6$-alkyl groups may in turn also be substituted by halogen atoms, such as F, Cl, Br or I, in particular F or Cl, or by —OH, —OR', —CN, —C(O)OH, —C(O)NR'$_2$, —SO$_2$NR'$_2$, —C(O)X, —SO$_2$OH, —SO$_2$X, —NO$_2$.

In the substituents R, $R^2$ to $R^{13}$ or $R^{1'}$ to $R^{4'}$, one or two non-adjacent carbon atoms which are not bonded in the α-position to the heteroatom may also be replaced by atoms and/or atom groups selected from the group —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$═N— or —P(O)R'—, where R'=non-, partially or perfluorinated C$_1$- to C$_6$-alkyl, C$_3$- to C$_7$-cycloalkyl or unsubstituted or substituted phenyl.

Without restricting generality, examples of substituents R, R$^2$ to R$^{13}$ and R$^{1'}$ to R$^{4'}$ modified in this way are:
—OCH$_3$, —OCH(CH$_3$)$_2$, —CH$_2$OCH$_3$, —CH$_2$—CH$_2$—O—CH$_3$, —C$_2$H$_4$OCH(CH$_3$)$_2$, —C$_2$H$_4$SC$_2$H$_5$, —C$_2$H$_4$SCH(CH$_3$)$_2$, —S(O)CH$_3$, —SO$_2$CH$_3$, —SO$_2$C$_6$H$_5$, —SO$_2$C$_3$H$_7$, —SO$_2$CH(CH$_3$)$_2$, —SO$_2$CH$_2$CF$_3$, —CH$_2$SO$_2$CH$_3$, —O—C$_4$H$_8$—O—C$_4$H$_9$, —CF$_3$, —C$_2$F$_5$, —C$_3$F$_7$, —C$_4$F$_9$, —C(CF$_3$)$_3$, —CF$_2$SO$_2$CF$_3$, —C$_2$F$_4$N(C$_2$F$_5$)C$_2$F$_5$, —CHF$_2$, —CH$_2$CF$_3$, —C$_2$F$_2$H$_3$, —C$_3$FH$_6$, —CH$_2$C$_3$F$_7$, —C(CFH$_2$)$_3$, —CH$_2$C(O)OH, —CH$_2$C$_6$H$_5$, —C(O)C$_6$H$_5$ or P(O)(C$_2$H$_5$)$_2$.

In R', C$_3$- to C$_7$-cycloalkyl is, for example, cyclopropyl, cyclobutyl, cyclopentyl, cyclohexyl or cycloheptyl.

In R', substituted phenyl denotes phenyl which is substituted by C$_1$- to C$_6$-alkyl, C$_1$- to C$_6$-alkenyl, NO$_2$, F, Cl, Br, I, OH, C$_1$-C$_6$-alkoxy, SCF$_3$, SO$_2$CF$_3$, COOH, SO$_2$X', SO$_2$NR''$_2$ or SO$_3$H, where X' denotes F, Cl or Br, and R'' denotes a non-, partially or perfluorinated C$_1$- to C$_6$-alkyl or C$_3$- to C$_7$-cycloalkyl as defined for R', for example o-, m- or p-methylphenyl, o-, m- or p-ethylphenyl, o-, m- or p-propylphenyl, o-, m- or p-isopropylphenyl, o-, m- or p-tert-butylphenyl, o-, m- or p-nitrophenyl, o-, m- or p-hydroxyphenyl, o-, m- or p-methoxyphenyl, o-, m- or p-ethoxyphenyl, o-, m- or p-(trifluoromethyl)-phenyl, o-, m- or p-(trifluoromethoxy)phenyl, o-, m- or p-(trifluoromethylsulfonyl)phenyl, o-, m- or p-fluorophenyl, o-, m- or p-chlorophenyl, o-, m- or p-bromophenyl, o-, m- or p-iodophenyl, furthermore preferably 2,3-, 2,4-, 2,5-, 2,6-, 3,4- or 3,5-dimethylphenyl, 2,3-, 2,4-, 2,5-, 2,6-, 3,4- or 3,5-di-hydroxyphenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-di-bromophenyl, 2,3-, 2,4-, 2,5-, 2,6-, 3,4- or 3,5-dimethoxyphenyl, 5-fluoro-2-methylphenyl, 3,4,5-trimethoxyphenyl or 2,4,5-trimethylphenyl.

In R$^{1'}$ to R$^{4'}$, heteroaryl is taken to mean a saturated or unsaturated mono-or bicyclic heterocyclic radical having 5 to 13 ring members, in which 1, 2 or 3 N and/or 1 or 2 S or O atoms may be present and the heterocyclic radical may be mono- or polysubstituted by C$_1$- to C$_6$-alkyl, C$_1$- to C$_6$-alkenyl, NO$_2$, F, Cl, Br, I, OH, C$_1$-C$_6$-alkoxy, SCF$_3$, SO$_2$CF$_3$, COOH, SO$_2$X', SO$_2$NR''$_2$ or SO$_3$H, where X' and R'' have a meaning indicated above.

The heterocyclic radical is preferably substituted or unsubstituted 2- or 3-furyl, 2- or 3-thienyl, 1-, 2- or 3-pyrrolyl, 1-, 2-, 4- or 5-imidazolyl, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -4- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-1 H-indolyl, 1-, 2-, 4- or 5-benzimidazolyl, 1-, 3-, 4-, 5-, 6- or 7-benzopyrazolyl, 2-, 4-, 5-,6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 1-, 2-, 3-, 4-, 5-, 6-, 7- or 8-quinolinyl, 1-, 3-, 4-, 5-, 6-, 7- or 8-isoquinolinyl, 1-, 2-, 3-, 4- or 9-carbazolyl, 1-, 2-, 3-, 4-, 5-, 6-, 7-, 8- or 9-acridinyl, 3-, 4-, 5-, 6-, 7- or 8-cinnolinyl, 2-, 4-, 5-, 6-, 7- or 8-quinazolinyl or 1-, 2- or 3-pyrrolidinyl.

Heteroaryl-C$_1$-C$_6$-alkyl is, analogously to aryl-C$_1$-C$_6$-alkyl, taken to mean, for example, pyridinylmethyl, pyridinylethyl, pyridinylpropyl, pyridinylbutyl, pyridinylpentyl or pyridinylhexyl, where the heterocycles described above may furthermore be linked to the alkylene chain in this way.

HetN$^+$ is preferably

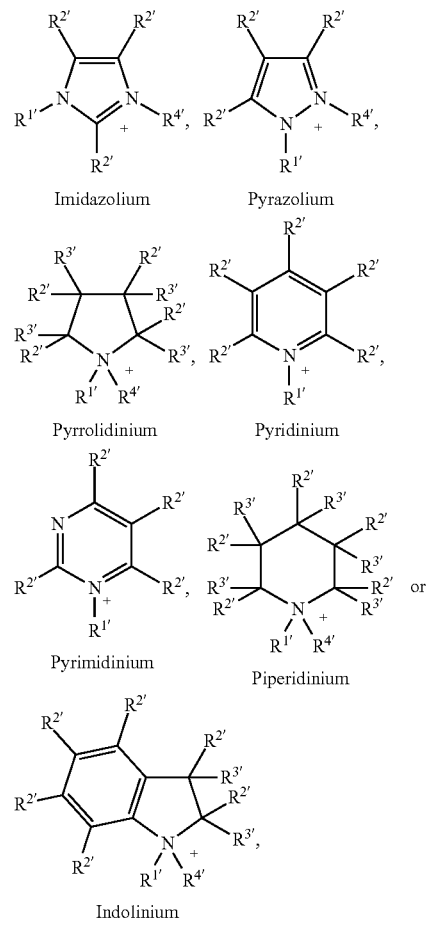

Imidazolium  Pyrazolium

Pyrrolidinium  Pyridinium

Pyrimidinium  Piperidinium  or

Indolinium where the substituents R$^{1'}$ to R$^{4'}$ each, independently of one another, have a meaning described above.

The cations of the chemical compound, preferably the ionic liquid, according to the invention are preferably ammonium, phosphonium, guanidinium or heterocyclic cations, particularly preferably ammonium or heterocyclic cations (HetN$^+$), preferably with the given structural formulae and substituents as described above. HetN$^+$ is particularly preferably imidazolium, pyrrolidinium or pyridinium, as defined above, where the substituents R$^{1'}$ to R$^{4'}$ each, independently of one another, have a meaning described above. HetN$^+$ is very particularly preferably imidazolium, where the substituents R$^{1'}$ to R$^{4'}$ each, independently of one another, have a meaning described above.

The present invention likewise relates to processes for the production of chemical compounds comprising a [X(CHR$^a$)$_n$—CH(R$^a$)SO$_3$]$^-$ anion comprising the step of reacting a compound with an anion X with a compound of formula I

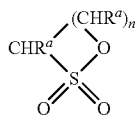

with n is 1-3
X is F, Cl, Br, $R^b$—C(O)O
$R^a$ is H, $C_{1-12}$-alkyl
$R^b$ is $C_{1-12}$-alkyl.

Preferably n is 2 or 3, particular preferably n is 3.

$R^a$ is preferably H or $C_{1-4}$ alkyl, particular preferably H.

$R^b$ is preferably $C_{1-8}$ alkyl, particular preferably methyl, ethyl, propyl, isopropyl, n-butyl, sec-butyl or tert-butyl.

Preferably, the compound with an anion X is a compound of formula $Kt^+X^-$ in which $Kt^+$ is a non-metallic cation or $K^+$, $Na^+$, $Rb^+$, $Cs^+$. The synthesis of Chloroalkylsulfonates is further described in detail after "Examples" what can be read in the broadest possible sense as part of the general description. Chemical compounds obtainable via the process of claim 1 in which X is Cl are particularly preferred.

The further functionalization with other nucleophiles such as alcoholates, phenolates, thiolates, thiophenolates, amides, malonates, phosphides, phosphates is of high practical relevance as the obtained chloroalkylsulfonates may act as starting materials for further anion functionalization. The ring opening reaction of sultones with other organic salts carrying nucleophilic anions directly is also possible. This mean that the compound with an anion X according to the invention can be further a compound with an anion Nu, as defined below.

Therefore, the present invention likewise relates to processes for the production of chemical compounds comprising a $[Nu(CHR^a)_n—CH(R^a)SO_3]^-$ anion comprising the step of reacting a compound with an anion Nu with a compound of formula I

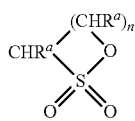

with n is 1-3
Nu is $OR^o$, OAr, $SR^o$, SAr, $NHR^o$, $N(R^o)_2$, $CH(COOR^o)_2$, $P(R^o)_2$, $P(Ar)_2$, $P(O)(OR^o)_2$
$R^a$ is H, $C_{1-12}$-alkyl
$R^b$ is $C_{1-12}$-alkyl.
$R^o$ is $C_{1-12}$-alkyl
Ar is a unsubstituted or substituted aromatic ring.

However, the process according to the invention can additionally be modified wherein X as being Cl or Br is substituted in a nucleophilic substitution reaction with alcoholates, phenolates, thiolates, thiophenolates, amides, malonates, phosphides, phosphates to form chemical compounds of formula II $Kt^+[Nu(CHR^a)_n—CH(R^a)SO_3]^-$   II wherein
$Kt^+$ is a non-metallic cation or $K^+$, $Na^+$, $Rb^+$, $Cs^+$
Nu is $OR^o$, OAr, $SR^o$, SAr, $NHR^o$, $N(R^o)_2$, $CH(COOR^o)_2$, $P(R^o)_2$, $P(Ar)_2$ $P(O)(OR^o)_2$
$R^o$ is $C_{1-12}$-alkyl Ar is a unsubstituted or substituted aromatic ring.

$R^o$ is preferably $C_{1-4}$-alkyl, particular preferably methyl, ethyl, propyl, isopropyl, n-butyl, sec-butyl or tert-butyl.

Ar is preferably unsubstituted or substituted phenyl as described below, particular preferably phenyl.

The second object of the invention are compounds of formula III $Kt^+[Y(CHR^a)_n—CH(R^a)SO_3]^-$   III with
$R^a$ is H, $C_{1-12}$-alkyl
$R^b$ is $C_{1-12}$-alkyl
and
$Kt^+$ is a non-metallic cation or $K^+$, $Na^+$, $Rb^+$, $Cs^+$
Y is F, Cl, Br, $R^b$—C(O)O or Nu
Nu is $OR^o$, OAr, $SR^o$, SAr, $NHR^o$, $N(R^o)_2$, $CH(COOR^o)_2$, $P(R^o)_2$, $P(Ar)_2$ $P(O)(OR^o)_2$
$R^o$ is $C_{1-12}$-alkyl
Ar is unsubstituted or substituted aromatic ring.

$Kt^+$, $R^a$, $R^b$, Y, Nu, $R^o$ and Ar can also have the preferred meanings as indicated above or below.

Nu is preferably $OR^o$, OAr, $SR^o$, SAr, $NHR^o$, $N(R^o)_2$, $P(R^o)_2$ or $P(Ar)_2$.

Y is particularly preferably Cl, Br or F, especially preferably Cl or F.

The process for the synthesis of compounds of formula III, in which Y is Cl or Br can be described by the following scheme 1, wherein $Kt^+$ means preferably non-metallic cations as described above and X is Cl or Br: This kind of reaction is described in detail within "Examples" and documented in the compounds of examples 1 to 3.

Scheme 1

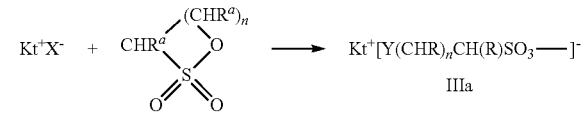

The process for the synthesis of compounds of formula III, in which X is F can be described by the one-pot synthesis of scheme 2 or the two step synthesis of scheme 3:

Scheme 2

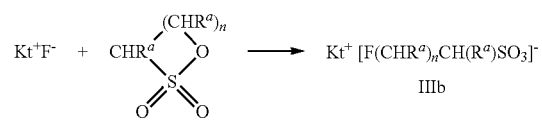

In scheme 2, the substituents are as defined above, e.g. $Kt^+=K^+$, $Na^+$, $Rb^+$, $Cs^+$ or non-metallic cation as described above $R^a$=H or $C_1$ bis $C_{12}$ Alkyl or substituted Alkyl, preferably butyl, n is 1 to 3.

Scheme 3

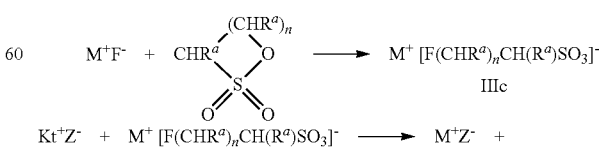

In scheme 3, the substituents are as defined:

$M^+=K^+, Na^+, Rb^+, Cs^+$ or non-metallic cation excluded the cation which will be used in the second step which is a classical metathesis reaction;

$Kt^+$ as defined in scheme 2 but not $M^+$.

$Z^-$ is any possible anion known in the field of ionic liquids, e.g. $[HSO_4]^-$, $[SO]^{2-}$, $[NO_3]^-$, $[BF_4]^-$, $[(R_F)BF_3]^-$, $[(R_F)_2BF_2]^-$, $[(R_F)_3BF]^-$, $[(R_F)_4B]^-$, $[B(CN)_4]^-$, $[PO_4]^{3-}$, $[HPO_4]^{2-}$, $[H_2PO_4]^-$, $[Alkyl\text{-}OPO_3]^{2-}$, $[(Alkyl\text{-}O)_2PO_2]^-$, $[Alkyl\text{-}PO_3]^{2-}$, $[R_FPO_3]^{2-}$, $[(Alkyl)_2PO_2]^-$, $[(R_F)_2PO_2]^-$, $[R_FSO_3]^-$, $[HOSO_2(CF_2)_pSO_2O]^-$, $[OSO_2(CF_2)_pSO_2O]^{2-}$, $[Alkyl\text{-}SO_3]^{3-}$, $[HOSO_2(CH_2)_pSO_2O]^-$, $[OSO_2(CH_2)_pSO_2O]^{2-}$, $[Alkyl\text{-}OSO_3]^-$, $[Alkyl\text{-}C(O)O]^-$, $[HO(O)C(CH_2)_pC(O)O]^-$, $[R_FC(O)O]^-$, $[HO(O)C(CF_2)_pC(O)O]^-$, $[O(O)C(CF_2)_pC(O)O]^{2-}$, $[(R_FSO_2)_2N]^-$, $[(FSO_2)_2N]^-$, $[((R_F)_2P(O))_2N]^-$, $[(R_FSO_2)_3C]^-$, $[(FSO_2)_3C]^-$, $Cl^-$ or $Br^-$ wherein alkyl is $C_1$ to $C_{12}$ alkyl, p is 1 to 8 and $R_F$ is fuorinated alkyl $(C_mF_{2m-x+1}H_x)$ with m=1-12 and x=0 to 7, wherein for m=1 x should be 0 to 2.

When a metallic cation, e.g. $K^+$, $Na^+$, $Rb^+$, $Cs^+$ is used as $M^+$, the anion is particularly preferably $Cl^-$, $Br^-$, $[Alkyl\text{-}SO_3]^-$ or $[Alkyl\text{-}SO_4]^-$. When a non-metallic cation, e.g. preferably ammonium cations as described in formula (1) is used as $M^+$, the anion is particularly preferably bis(trifluoromethylsulfonyl)imide.

The conditions of the metathesis reaction is well-known to the person skilled in the art. An example is given in example 5 below.

The process for the synthesis of compounds of formula III in which X is Nu can be described by the following scheme 4:

Scheme 4

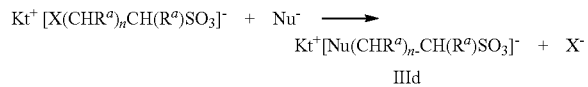

$$Kt^+[X(CHR^a)_nCH(R^a)SO_3]^- + Nu^- \longrightarrow Kt^+[Nu(CHR^a)_n\text{-}CH(R^a)SO_3]^- + X^-$$

IIId

The substituents in scheme 4 are defined as

X is Cl, Br, n=1 to 3, $R^a$ as defined in the schemes above,

Nu is $OR^o$, OAr, $SR^o$, SAr, $NHR^o$, $N(R^o)_2$, $CH(COOR^o)_2$, $P(R^o)_2$, $P(Ar)_2$, $P(O)(OR^o)_2$ with $R^o$ and Ar as defined above.

Reactions are described in examples 7 and 9 to 13.

However this reaction according to scheme 4 can be used additionally for the synthesis of chemical compounds with an anion $[F(CHR^a)_nCH(R^a)SO_3]^-$, in that F is used as $Nu^-$, as described in example 6.

However this reaction according to scheme 4 can be used additionally for the synthesis of chemical compounds with an anion $[R^b\text{—}C(O)O(CHR^a)_nCH(R^a)SO_3]^-$, in that $R^b\text{—}C(O)O^-$ is used as $Nu^-$, as described in example 8.

Ar means a substituted or unsubstituted aromatic ring with 6 to 18 C atoms, e.g. phenyl, naphthyl or anthracenyl, which may be substituted by $C_1$- to $C_6$-alkyl, $C_1$- to $C_6$-alkenyl, $NO_2$, F, Cl, Br, I, OH, $C_1$-$C_6$-alkoxy, $SCF_3$, $SO_2CF_3$, COOH, $SO_2X'$, $SO_2NR''_2$ or $SO_3H$, where X' denotes F, Cl or Br, and R'' denotes a non-, partially or perfluorinated $C_1$- to $C_6$-alkyl or $C_3$- to $C_7$-cycloalkyl as defined for R' above.

Substituted phenyl as Ar is for example o-, m- or p-methylphenyl, o-, m- or p-ethylphenyl, o-, m- or p-propylphenyl, o-, m- or p-isopropylphenyl, o-, m- or p-tert-butylphenyl, o-, m- or p-nitrophenyl, o-, m- or p-hydroxyphenyl, o-, m- or p-methoxyphenyl, o-, m- or p-ethoxyphenyl, o-, m- or p-(trifluoromethyl)phenyl, o-, m- or p-(trifluoromethoxy)phenyl, o-, m- or p-(trifluoromethylsulfonyl)phenyl, o-, m- or p-fluorophenyl, o-, m- or p-chlorophenyl, o-, m- or p-bromophenyl, o-, m- or p-iodophenyl, furthermore preferably 2,3-, 2,4-, 2,5-, 2,6-, 3,4- or 3,5-dimethylphenyl, 2,3-, 2,4-, 2,5-, 2,6-, 3,4- or 3,5-dihydroxyphenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3-, 2,4-, 2,5-, 2,6-, 3,4- or 3,5-dimethoxyphenyl, 5-fluoro-2-methylphenyl, 3,4,5-trimethoxyphenyl or 2,4,5-trimethylphenyl.

The reactions typically can be carried out at temperatures in the range from 0 to 150° C., preferably at 0 to 50° C. and in particular at room temperature.

Suitable solvents or solvent mixtures for the inventive process according to claim 1 or as described for the direct reaction with a nucleophile are for example water, alcohols, dialkyl ethers, esters, nitriles, dialkyl carbonates, dichloromethane or mixtures thereof. The solvent is preferably methanol, ethanol, i-propanol, acetonitrile, propionitrile, diethyl ether, 1,2-dimethoxyethane, dimethyl carbonate or diethyl carbonate. However, it is possible to carry out the inventive process without any solvent. It is preferred to avoid the use of a solvent when the starting materials are liquid under the reaction conditions or when the reaction mixture is liquid under the reaction conditions.

In the inventive process, the ratio of the compound with an anion X or Nu to the compound of formula I is 1:1 to 1:50, preferably 1:1.05 to 1:20.

The functionalized ionic liquids according to this invention are characterized by the fact that they combine the beneficial properties of alkylsulfonate ionic liquids, such as high thermal and hydrolytic stability, attractive viscosities and low melting points with the task-specific properties of the functionality introduced by the groups X or Nu in a unique manner. Depending on the nature of the introduced functionality X or Nu the new ionic liquids display unique coordination properties to metals, unique viscosity properties, unique gas solubility properties, unique lubrication behavior, unique solvation properties or unique phase behavior. For example the introduction of phosphine, amine or thioether groups via the group Nu allows very specific and unique interactions to metals while the introduction of the ether groups will decrease the ionic liquid's viscosity. The process to synthesize the new ionic liquids according to this invention is straight forward and suitable for up-scaling which is a great advantage over traditional routes to synthesize ionic liquids with functionalized anions.

Preferred chemical compounds of formula III, as described above, do not show signs of decomposition even after 12 hours in the presence of an excess of water at 100° C. and can be seen as very stable against hydrolysis.

The present invention furthermore relates to the use of the said ionic liquids as solvent or solvent additive, as phase-transfer catalyst, as extractant, as heat-transfer medium, as surface-active substance, as plasticiser, as flame retardant, as conductive salt or additive in electrochemical cells.

In the case of the use of the said ionic liquids as solvents, these are suitable in any type of reaction known to the person skilled in the art, for example for transition-metal- or enzyme-catalysed reactions, such as, for example, hydroformylation reactions, oligomerisation reactions, esterifications or isomerisations, where the said list is not exhaustive.

On use as extractant, the ionic liquid can be employed to separate off reaction products, but also to separate off impurities, depending on the solubility of the respective component in the ionic liquid. In addition, the ionic liquids may also serve as separation media in the separation of a plurality of components, for example in the distillative separation of a plurality of components of a mixture.

Further possible applications are use as plasticiser in polymer materials, as flame retardant for a number of materials or applications, and as conductive salt or additive in various electrochemical cells and applications, for example in galvanic cells, in capacitors or in fuel cells.

Further fields of applications of the new chemical compounds, e.g. ionic liquids, according to this invention are solvents for carbohydrate containing solids in particular biopolymers and derivatives or degredation products thereof. In addition, these new compounds can be applied as lubricants, working fluids for maschines, such as compressors, pumps or hydraulic devices. The ionic liquids according to this invention may be also used in electro-chemical cells in particular for electo-optical cells, as functional materials in sensors. A further field of application that relies in particular on the nature of the functionalization of the anion by the group Nu is in the field of particle or nanomaterial synthesis where these ionic liquids can act as medium or additive.

Even without further comments, it is assumed that a person skilled in the art will be able to utilise the above description in the broadest scope. The preferred embodiments and examples should therefore merely be regarded as descriptive disclosure which is absolutely not limiting in any way. On the other hand the description of the specific examples can be generalized by on skilled in the art.

EXAMPLES

The reactions of 1,4-butane sultone with both 1,3-dialkylimidazolium chlorides and an tetraethylammonium chloride are displayed in Scheme A: Reaction of 1,3-dialkylimidazolium chlorides and tetraethylammonium chloride with 1,4 butane sultone to form the corresponding chlorobutylsulfonate ionic liquids:

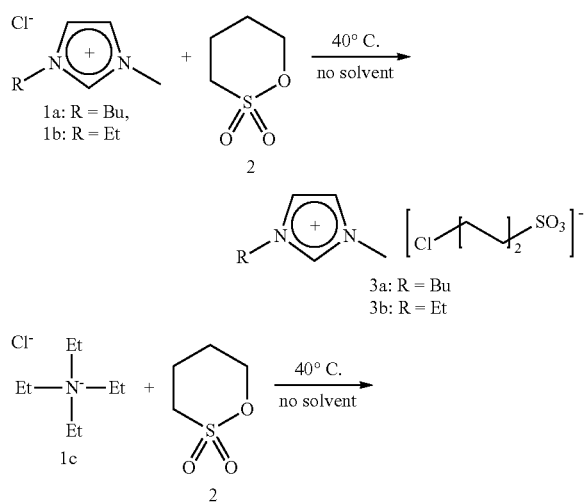

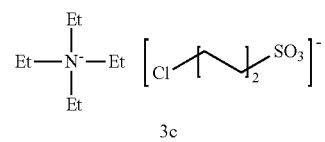

Bu means butyl, Et means ethyl.

The reaction builds on the known ability of sultones to react in a ring-opening reaction with various nucleophiles. In the past, the ring opening reaction of sultones with amines has also been applied to obtain ammonium ions, e.g. in A. C. Cole et al, J. Am. Chem. Soc., 2002, 124, 5962.

In the case the chloride ion of an organic salt being the nucleophile the reaction proceeds smoothly to full conversion under mild conditions if an excess of the sultone is applied (20 eq.). After the reaction the excess of sultone is removed by distillation or extraction (recovered sulton can be used for the next synthetic batch) and the anion functionalized chemical compound, e.g. preferably the anion functionalized ionic liquid, is isolated in quantitative yield. By titration with $AgNO_3$ it could be confirmed that the chloroalkylsulfonate salts obtained in this way are essentially free of chloride impurities (<200 ppm Cl$^-$) which is of great advantage compared to the traditional metathesis routes.

FIG. 1 shows results of detailed kinetic investigations of the synthesis of 1-butyl-3-methylimidazolium [BMIM] 4-chlorobutylsulfonate at different temperatures with the ratio [BMIM]Cl:1,4-butane sultone being 1:20 in the solvent nitroethane.

From this study it was found that the reaction rate is pseudo first order both in [BMIM]Cl and in 1,4-butane sultone. The activation energy of the ring opening reaction was found to be 79 KJ/mol. Interestingly, similar experiments reacting [BMIM]Cl with 1,3-propane sultone revealed a much higher reaction rate for the five-membered sultone compared to the six-membered sultone. Under the same reaction conditions as illustrated in FIG. 1, the 1,3-propane sultone reached full conversion in less than 10 minutes at 30° C. (for comparison: the reaction with 1,4-butane sultone showed only 12% conversion after 10 min at 30° C.). These results demonstrate impressively the synthetic value of the here described reaction for the preparation of anion functionalized chemical compounds.

All chloroalkylsulfonates are obtained as colorless liquids if the chloride salt starting material is colorless, too. All products are remarkably water soluble and hydrolysis stable at the temperature conditions applied (up to 60° C.).

For further investigation of their physico-chemical properties, the chloroalkylsulfonate ionic liquids as described in Examples 1 to 3 were dried overnight at 50° C. in high vacuum (1*10$^{-3}$ mbar). After this treatment, water contents were still surprisingly high for the imidazolium based chloroalkylsulfonates indicating their strong ability to interact with water. Table 1 shows the viscosities of selected chloroalkylsulfonates obtained in this way. Ionic liquids 3a-c were found to behave like Newtonion fluids. The displayed viscosity results were obtained from 20 different shearing rates between 1 s$^{-1}$ and 1000 s$^{-1}$ at 20° C.

Viscosities of selected chloroalkylsulfonates

| chemical compound | water content/ppm | gtp[1]/° C. | Viscosity (20° C.)/mPa s |
|---|---|---|---|
| [EMIM][ClC$_4$H$_8$SO$_3$] (3b) | 1462 | −65.7 | 648 |
| [BMIM][ClC$_4$H$_8$SO$_3$] (3a) | 1969 | −63.9 | 800 |
| [NEt$_4$][ClC$_4$H$_8$SO$_3$] (3c) | 340 | −46.5 | 5250 |

[1]gtp = glass transition point

Ionic liquids 3a-c are liquids at room temperature. Their glass transition points have been determined by DSC (see supporting information for details). The fact that even 3c forms a liquid at room temperature is remarkable in this context since other tetraethylammonium salts—even those with anions that are well known to form low-melting ionic liquids—show much higher melting points. For example, [NEt$_4$][NTf$_2$] was found to melt at 109° C., the melting point of [NEt$_4$][CF$_3$SO$_3$] has been determined to be 162° C. This comparison demonstrates the ability of the chloroalkylsulfonate anion to lead to low melting salts, at least for highly symmetrical ammonium cations.

In order to make sure that the ionic liquids as described above were of very high purity we decided to use also an IL surface sensitive analytical technique. X-Ray photoelectron spectroscopy (AR-XPS) was recently established as a very suitable method to determine impurities down to an extremely low level if those impurities show at least some surface activity in the ionic liquid system. Consequently, the chemical composition and the electronic structure of the freshly prepared ionic liquid [BMIM][ClC$_4$H$_8$SO$_3$] was characterized by angle resolved XPS under ultra high vacuum (UHV) conditions. Since the inelastic mean free path of photoelectrons of organic compounds is ~3 nm, measurements at 0° (normal emission) probe the surface near region (information depth, ID: 7-9 nm) whereas measurements at 70° only probe the topmost layers (ID: 2-3 nm). The XPS data in FIG. 2 show the expected signals of C, N, O, S, and Cl, with no sign of other elements, ruling out surface contaminations of e.g. Si-containing impurities, which were observed for other ionic liquids in the past (probably from grease and sealings).

Figure 2:
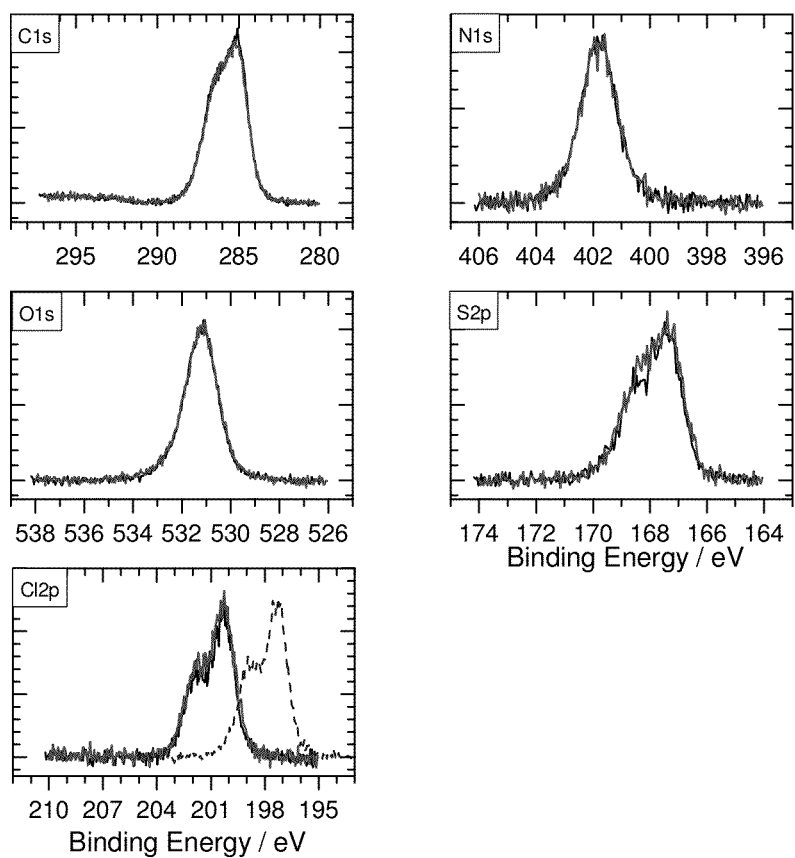

FIG. 2: AR-XP spectra of 3a ([BMIM][ClC$_4$H$_8$SO$_3$]) in the C1s, N1s, O1s, S2p, and Cl2p regions. The spectra were collected at emission angles of 0° (black, bulk sensitive) and 70° (surface sensitive). In the Cl region, a chloride spectrum of [EMIM]Cl (right spectrum) is added for comparison. [EMIM] means ethyl-methyl-imidazolium.

For all Ionic Liquid-related core levels, no significant changes of intensity with emission angle were observed, which is an indication for a homogeneous distribution of the elements within the near surface region. It also rules out pronounced preferential vertical orientation of Ionic Liquid molecules at the surface, as was described for [BMIM][BF$_4$] by AR-XPS. The quantitative evaluation of the XPS signals in both geometries yields a composition of C:N:O:S:Cl=12.1: 2.0:3.0:1.0:0.9 which is in good agreement with the expected stoichiometry of 12:2:3:1:1. Finally, no signals related to residual chloride ions from the synthesis reaction could be observed, confirming a complete conversion of the chloride Ionic Liquid.

For comparison, the Cl2p spectrum of [EMIM]Cl is added in FIG. 2 (left bottom, right side), showing the chloride signal to be shifted to lower binding energies by about 3 eV in comparison to the Cl-sulfonate signal. As expected, the Cl binding energy position of the chloroalkylsulfonate (200.3 eV, Cl 2p$_{3/2}$) is in the range of neutral Cl-alkyl species (e.g., polyvinylchloride 200.0-200.6 eV). Hence, it is likely that the negative charge in the anion is localized at the SO$_3$ group rather than in the vicinity of the Cl atom.

As the thermal stability is crucial for the use of the inventive compounds as being an ionic liquid, thermal gravimetric analyses (TGA) were carried out for 3a-c. The TGA measurements were performed in the range of 20° C. to 450° C. with a gradient of 10 K/min (see supporting information for details). 3a-c showed very similar weight losses in the TGA experiment with on-set temperatures of 214.9° C. (3a), 214.2° C. (3b) and 210.1° C. (3c), respectively. Interestingly, all three ionic liquids reached a plateau after a first decomposition step of which the weight loss corresponds to the loss of 1,4-butane sultone. After evaporation of the 1,4-butane sultone the remaining chloride ionic liquid decomposed at slightly higher temperatures under the conditions of these TGA measurements (on-set temperatures: 3a=294.4° C.; 3b=307.4° C.; 3c=269.7° C.). This decompostion pathway was also confirmed by keeping 3a for 4 h at 210° C. collecting the volatile components. After this treatment the volatile fraction contained significant amounts of 1,4 butane sultone and the remaining liquid consisted of mainly [BMIM]Cl (according to $^1$H-NMR analysis).

The retro-reaction affording the chloride ionic liquid was also confirmed by a special XPS experiment at 330 K. Under the UHV conditions of the XPS experiment (removal of the volatile sultone!) this temperature is obviously high enough to detect after several hours the appearance of a chloride signal next to the Cl-signal from the chloroalkylsulfonate ion (for details see supporting information) unambigiously proving the formation of chloride anions in the surface near volume of the ionic liquid.

In conclusion, the process according to the invention is a very convenient one-step synthesis to get compounds with chloroalkylsulfonate anions starting from commercial chloride ionic liquids. The resulting chloroalkylsulfonates exhibit a number of interesting physico-chemical properties but their thermal stability is limited by the retro-reaction to a practical application range below 150° C.

General synthesis of 1-alkyl-3-methylimidazolium or tetraethyl-ammonium chlorobutylsulfonate ionic liquids: 1-alkyl-3-methylimidazolium chlorides were obtained from Solvent Innovation GmbH, Cologne. 1,4-butane sultone and tetraethylammonium chloride were purchased from Aldrich 1.0 equiv. of an amine was weighed into a dry Schlenk flask and 20 equiv. of 1,4-butane sultone was added in small portions. The reaction mixture was stirred for 24 h time at 40° C. After removal of the 1,4-butane by extraction with dichloromethane, water phase was dried under reduce pressure and the product was isolated as a colorless viscous liquid.

The following examples illustrate the described method in detail

EXAMPLE 1

1-Butyl-3-methylimidazolium 4-chlorobutylsulfonate (3a)

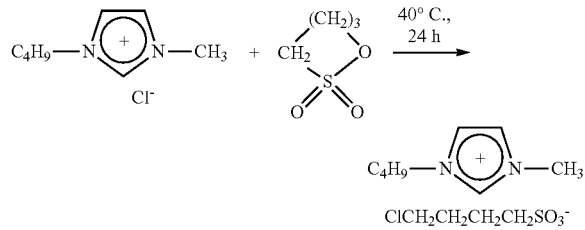

The mixture of equivalent of 1-butyl-3-methylimidazolium chloride and 20 equivalents of 1,4-butane sultone is stirred at 40° C. (temperature in the oil-bath) for 24 hours). The excess of 1,4-butane sultone was distilled off in vacuum and the residue was dried overnight at 50° C. in high vacuum ($1 \cdot 10^{-3}$ mbar). Liquid 1-butyl-3-methylimidazolium 4-chlorobutylsulfonate is obtained in close to quantitative yield. The material was characterized by NMR spectroscopy.

$^1$H NMR (Referenz Substance: TMS; Solvent: $CDCl_3$), δ, ppm: 0.72 (t, 3H, $CH_2CH_3$, J=7.37 Hz), 1.12 (m, 2H, $CH_3$ $\underline{CH}_2$), 1.60-1.67 (m, 2H, $\underline{CH}_2CH_2N$), 1.67-1.78 (m, 4H, $\underline{CH}_2CH_2$), 2.62 (t, 2H, $ClCH_2$, J=7.53 Hz), 3.33 (t, 2H, $SCH_2$, J=6.09 Hz), 3.81 (s, 3H, $NCH_3$), 4.04 (t, 2H, $NCH_2$, J=7.37 Hz), 7.29 (s, 1H, $NCHCH$), 7.41 (s, 1H, $NCHCH$) and 9.56 (s, 1H, $NCHN$).

$^{13}$C NMR (Referenz Substance: TMS; Solvent: $CDCl_3$), δ, ppm: 13.05 ($\underline{CH}_2CH_3$), 19.02 ($CH_3\underline{CH}_2$), 22.61 ($Cl\underline{CH}_2$ $CH_2$), 31.28 ($CH_2\underline{CH}_2$), 31.72 ($SCH_2\underline{CH}_2$), 35.93 ($CH_3N$), 44.55 ($Cl\underline{CH}_2$), 49.11 ($CH_2N$), 50.68 ($SCH_2$), 121.9 ($NCHCH$), 123.5 ($NCHCH$) and 137.3 ($NCHN$).

EXAMPLE 2

1-Ethyl-3-methylimidazolium 4-chlorobutylsulfonate (3b)

1-Ethyl-3-methylimidazolium 4-chlorobutylsulfonate is obtained in the similar to Example 1 procedure, isolated and characterized with NMR spectra.

$^1$H NMR (Referenz Substance: TMS; Solvent: DMSO-$d_6$), δ, ppm: 1.37 (t, 3H, $CH_2CH_3$, J=7.20 Hz), 1.61-1.77 (m, 4H, $CH_2CH_2$), 2.43 (t, 2H, $Cl\underline{CH}_2$, J=7.31 Hz), 3.56 (t, 2H, $SCH_2$, J=6.38 Hz), 3.83 (s, 3H, $NCH_3$), 4.17 (q, 2H, $NCH_2$, J=7.20 Hz), 7.74 (s, 1H, NCHCHN), 7.83 (s, 1H, NCHCHN) and 9.32 (s, 1H, NCHN).

$^{13}$C NMR (Referenz Substance: TMS; Solvent: DMSO-$d_6$), δ, ppm: 15.69 ($CH_3CH_2$), 23.18 ($ClCH_2CH_2$), 31.79 ($SCH_2CH_2$), 36.14 ($CH_3N$), 44.57 ($ClCH_2$), 45.92 ($CH_2N$), 51.08 ($SCH_2$), 122.5 (NCHCH), 124.1 (NCHCH) and 137.1 (NCHN).

EXAMPLE 3

Tetraethylammonium 4-chlorobutylsulfonate (3c)

Tetraethylammonium 4-chlorobutylsulfonate is obtained in the similar to Example 1 procedure, isolated and characterized with NMR spectra.

$^1$H NMR (Referenz Substance: TMS; Solvent: $CDCl_3$), δ, ppm: 1.18 (t, 12H, $CH_2CH_3$), 1.73-1.80 (m, 4H, $CH_2CH_2$), 2.62 (t, 2H, $ClCH_2$), 3.23 (q, 8H, $NCH_2$) and 3.39 (t, 2H, $SCH_2$).

$^{13}$C NMR (Referenz Substance: TMS; Solvent: $CDCl_3$), δ, ppm: 7.44 ($CH_3CH_2N$), 22.85 ($ClCH_2CH_2$), 31.53 ($SCH_2$ $\underline{CH}_2$), 44.85 ($Cl\underline{CH}_2$), 50.70 ($CH_2N$) and 52.26($SCH_2$).

All NMR spectra were recorded by Brucker NMR-spectrometr with the 400 MHz frequency for $^1$H and 100 MHz for $^{13}$C nuclear.

EXAMPLE 4

Synthesis of Tetrabutylammonium fluorobutylsulfonate [TBA][$FC_4H_8SO_3$]

Dry solvents, 1,4-Butylsultone, Tetrabutylammonium fluoride [TBA]F and 1-Ethyl-3-methylimidazolium bis(trifluoromethylsulfonyl)imide [EMIM][$Tf_2N$] were purchased as commercial products from different manufacturers (Aldrich, Merck, Solvent Innovation).

The described synthesis is carried out in an inert atmosphere. The Schlenkvessels used were torched in vacuum three times prior to use and fed by argon.

The nmr spectra were measured at room temperature with the spectrometer ECX 400 0f Jeol Company ($^1$H: 400 MHz, $^{13}$C: 100 MHz, $^{19}$F: 376 MHz) in DMSO-d6. The chemical shifts are stated in ppm and the coupling constants in Hz.

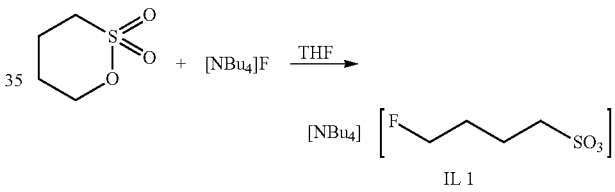

In a 100 ml Schlenkvessel 4.08 g (0.03 mol) 1,4-Butylsultone is dissolved in 30 ml tetrahydrofuran (absolute) and subsequently 5.22 g (0.02 mol) [TBA]F in THF is added. The mixture is stirred for 24 h in an Argon atmosphere at 30° Ct. The excess sultone is extracted from $H_2O$ and toluene. The aqueous phase is dried and the product is obtained as a white crystalline compound.

Yield: 6 g (0.015 mol), 75%.

NMR-DATA:

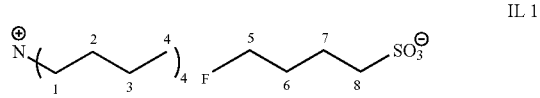

$^1$H-NMR (400 MHz, $CDCl_3$): δ=0.94 (t, H4, 3H, $J_{H-H}$=7.20 Hz); 1.39 (m, H3, 2H); 1.57 (m, H2, 2H); 1.75 (m, H6, 2H); 1.88 (m, H7, 2H); 2.77 (t, H8, 2H, $J_{H-H}$=7.41 Hz); 3.21 (t, H1, 2H, $J_{H-H}$=8.64 Hz); 4.32 (t, H5, 1H, $J_{H-H}$=6.17 Hz); 4.44 (t, H5, 1H, $J_{H-H}$=5.97 Hz, $J_{H-F}$=41.36 Hz) ppm.

$^{13}$C-NMR (100 MHz, $CDCl_3$): δ=13.59 (C-4); 19.59 (C-3); 21.40 (C-7); 23.83 (C-2); 29.57; 29.76 (C-6); 51.23 (C-8); 58.46 (C-1); 83.11; 84.74 (C-5) ppm.

$^{19}$F-NMR (376 MHz, $CDCl_3$): δ=−218.0 ppm.

EXAMPLE 5

Synthesis of 1-Ethyl-3-methylimidazolium fluorobutylsulfonate

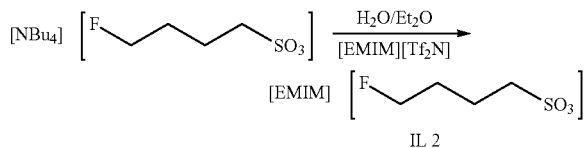

IL 2

In a 100 ml Schlenkvessel 3.00 g (0.0075 mol) Tetrabutylammonium fluorobutylsulfonate and the same amount diethyl ether is solved and 2.93 g (0.0075 mol) 1-Ethyl-3-methylimidazolium bis(trifluoromethyl-sulfonyl)imide is added. The organic phase with diethyl ether is separated and the remaining phase is washed with diethyl ether several times. Afterwards the product is liberated from the solvent under reduced pressure and a clear yellow liquid is obtained.

Yield: 1.8 g (0.0068 mol), 90%.

NMR-Data:

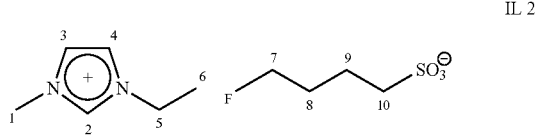

IL 2

$^{1}$H-NMR (400 MHz, CDCl$_3$): δ=1.46 (t, H6, 3H, $J_{H-H}$=7.20 Hz); 1.74 (m, H9, 2H); 1.86 (m, H8, 2H); 2.77 (t, H10, 2H, $J_{H-H}$=7.82 Hz); 3.93 (s, H1, 3H); 4.24 (q, H5, 2H); 4.30 (t, H7, 1H, $J_{H-H}$=6.17 Hz); 4.42 (t, H7, 1H, $J_{H-H}$=5.97 Hz, $J_{H-F}$=41.36 Hz); 7.41 (s, H4, 1H); 7.44 (s, H3, 1H); 9.75 (s, H2, 1H) ppm.

$^{13}$C-NMR (100 MHz, CDCl$_3$): δ=15.58 (C-6); 21.52 (C-9); 29.54; 29.74 (C-8); 36.33 (C-1); 45.06 (C-5); 51.42 (C-10); 83.12; 84.75 (C-7); 121.9 (C-4); 124.3 (C-3); 137.6 (C-2) ppm.

$^{19}$F-NMR (376 MHz, CDCl$_3$): δ=−218.6 ppm.

Properties of the Chemical Compounds According to Example 4 and 5

Determination of the Water Content:

The water content was measured via coulometric Karl-Fischer-titration. A Metrohm 756 KF Coulometer with a Hydranal® Coulomat AG reagent is used.

Determination of Melting-Points:

The determination of the melting-points is carried out with hermetically sealded samples of the compound; differential scanning calorimetry (DSC) on a Netzsch DSC 205 Phoenix spectrometer. The samples were cooled down to −140° C. and then heated up at a heating rate of 10 K/min. The melting points were determined via thermography.

Viscosity

The viscosity of the melted substances is measured under argon atmosphere with a MCR 100 rheometer of Anton Paar. The temperature control is performed with a Peltier device. All viscometry measurements of the substances were performed with a defined water content (250±15 Ppm).

Thermal Stability:

Thermogravitmetric measurements were performded with a Netzsch TG 209. In this connection the samples were used in open Al$_2$O$_3$ flash cups and heated up to 450° C. with 10 K/min. The TG-Onset temperature (decomposition temperature) is determined using thermograms.

| | H$_2$O [ppm] | mp$^a$/° C. | T$_{dec}$$^c$/° C. | η$^d$ bei 60° C./ mPa * s |
|---|---|---|---|---|
| (TBA)[FC$_4$H$_8$SO$_3$] | 235 | 45.0 –45.8$^b$ | 257.5 | 370* |
| [EMIM][FC$_4$H$_8$SO$_3$] | 259 | −71.6$^b$ | 296.4 | 51.4** |

$^a$Melting point;
$^b$Glass-transiton temperature;
$^c$Decomposition TG-onset, 10K/min,
$^d$Viscosity,
*Newtonian behaviour,
**not-Newtonian behaviour

[TBA][FC$_4$H$_8$SO$_3$] white crystals. The melting point is 45° C. and is unusually low for ammonium-cation.

[EMIM][FC$_4$H$_8$SO$_3$] is a light yellow liquid that shows variances of Newtonian behaviour.

EXAMPLE 6

Synthesis of 1-Butyl-3-methylimidazolium fluorobutylsulfonate [BMIM][FC$_4$H$_8$SO$_3$] (IL 4)

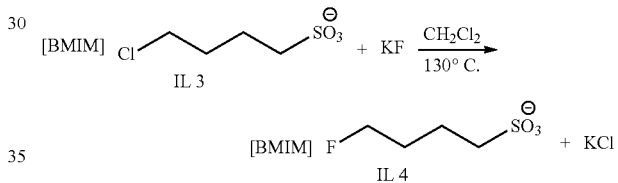

1-Butyl-3-methylimidazolium chlorobutylsulfonate (1.0 eqiv.) is heated with potassium fluoride (5.0 equiv.) at 130° C. for 24 h (Finkelstein reaction). After cooling to 10° C. dichloromethane is added and the potassium salts are separated by filtration. The organic solvent is evaporated under reduce pressure and the product is obtained as a yellow liquid (conversion 36.5%).

EXAMPLE 7

Synthesis of 1-Butyl-3-methylimidazolium ethoxybutylsulfonate

[BMIM][EtOC$_4$H$_8$SO$_3$] (IL 5)

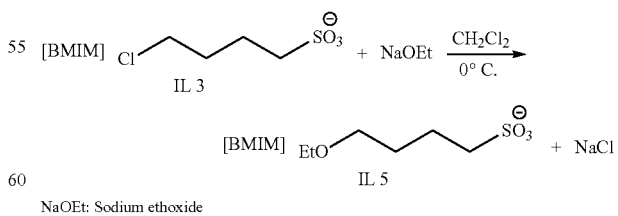

NaOEt: Sodium ethoxide

1-Butyl-3-methylimidazolium chlorobutylsulfonate (1.0 eqiv.) are slowly added to a solution of sodium ethoxide (1 equiv.) in 20 ml THF that is pre-cooled to 0° C. in an external cooling bath. After 4 h of stirring under argon atmosphere the mixture is heated up to 40° C. and is stirred under argon for another 6 h. After cooling to 10° C. the sodium salt is separated by filtration. The product is obtained in the form of a slightly yellowish liquid (conversion 50.0%).

The following compounds can be synthesized accordingly:
N-Butyl-pyridinium ethoxybutylsulfonate,
N-Ethyl-pyridinium ethoxybutylsulfonate,
N-Methyl-N-butyl-pyrrolidinium ethoxybutylsulfonate,
N-Methyl-N-ethyl-pyrrolidinium ethoxybutylsulfonate,
Tetrabutylammonium ethoxybutylsulfonate,
N-Butyl-pyridinium propoxybutylsulfonate,
N-Ethyl-pyridinium propoxybutylsulfonate,
N-Methyl-N-butyl-pyrrolidinium propoxybutylsulfonate,
N-Methyl-N-ethyl-pyrrolidinium propoxybutylsulfonate,
Tetrabutylammonium propoxybutylsulfonate.

EXAMPLE 8

Synthesis of 1-Butyl-3-methylimidazolium acetobutylsulfonate [BMIM][AcC$_4$H$_8$SO$_3$] (IL 6)

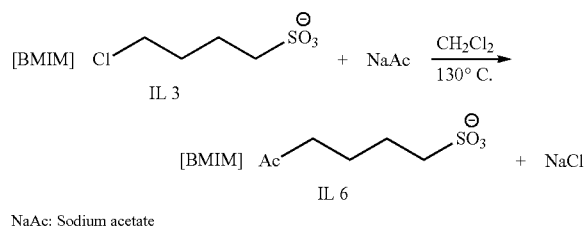

NaAc: Sodium acetate

1-Butyl-3-methylimidazolium 4-chlorobutylsulfonate (1.0 eqiv.) is heated with sodium acetate (1.3 equiv.) at 70° C. for 24 h. After cooling to 10° C. dichloromethane is added and the sodium salts are separated by filtration. The organic solvent is evaporated under reduce pressure and the product is obtained as a colourless liquid (conversion 66.0%).

The following compounds can be synthesized accordingly:
N-Butyl-pyridinium acetobutylsulfonate,
N-Ethyl-pyridinium acetobutylsulfonate,
N-Methyl-N-butyl-pyrrolidinium acetobutylsulfonate,
N-Methyl-N-ethyl-pyrrolidinium acetobutylsulfonate,
Tetrabutylammonium acetobutylsulfonate.

EXAMPLE 9

Synthesis of Tetrabutylammonium-4-ethylthiobutylsulfonate

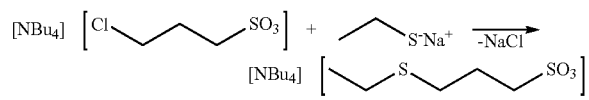

To a solution of tetrabutylammonium-4-chlorobutylsulfonate in THF (tetrahydrofuran) a solution of NaSEt in THF is added dropwise under cooling. After complete addition, the solution is allowed to warm to room temperature. The precipitate is filtered off and the remaining solution is concentrated with a rotary evaporator to yield tetrabutylammonium-4-ethylthiobutylsulfonate.

EXAMPLE 10

Synthesis of Tetrabutylammonium-4-phenoxybutylsulfonate

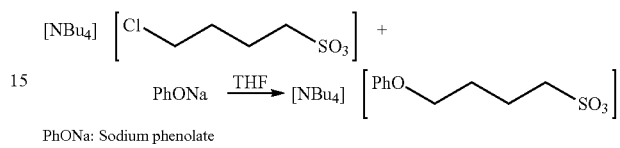

PhONa: Sodium phenolate

To a solution of tetrabutylammonium-4-chlorobutylsulfonate in THF a solution of sodium phenolate in THF is added dropwise under cooling. After complete addition, the solution is allowed to warm to room temperature. The precipitate is filtered off and the remaining solution is concentrated with a rotary evaporator to yield tetrabutylammonium-4-phenoxybutylsulfonate.

EXAMPLE 11

Synthesis of Tetrabutylammonium-4-dimethylaminobutylsulfonate

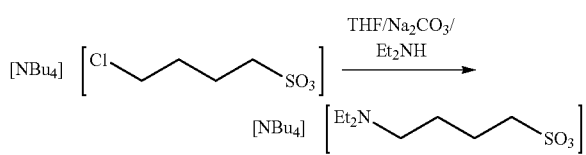

To a solution of tetrabutylammonium-4-chlorobutylsulfonate in THF sodium carbonate is added. To the resulting suspension, a solution of diethylamine in THF is added. The suspension is stirred at room temperature for 1 h. The precipitate is filtered off and the remaining solution is concentrated with a rotary evaporator to yield tetrabutylammonium-4-diethylaminobutylsulfonate.

The following compounds can be synthesized accordingly:
1-Butyl-3-methyl-imidazolium dimethylaminobutylsulfonate,
N-Butyl-pyridinium dimethylaminobutylsulfonate,
N-Ethyl-pyridinium dimethylaminobutylsulfonate,
N-Methyl-N-butyl-pyrrolidinium dimethylaminobutylsulfonate,
N-Methyl-N-ethyl-pyrrolidinium dimethylaminobutylsulfonate,
1-Butyl-3-methyl-imidazolium diethylaminobutylsulfonate,
N-Butyl-pyridinium diethylaminobutylsulfonate,
N-Ethyl-pyridinium diethylaminobutylsulfonate,
N-Methyl-N-butyl-pyrrolidinium diethylaminobutylsulfonate, N-Methyl-N-ethyl-pyrrolidinium diethylaminobutylsulfonate.

EXAMPLE 12

Synthesis of Tetrabutylammonium-4-diphenylphoshino-butylsulfonate

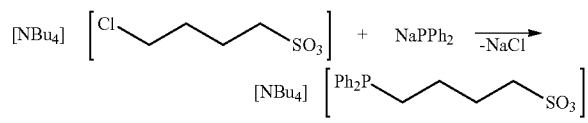

To a solution of tetrabutylammonium-4-chlorobutylsulfonate in THF a solution of NaPPh$_2$ in THF is added dropwise under cooling. After complete addition, the solution is allowed to warm to room temperature. The precipitate is filtered off and the remaining solution is concentrated with a rotary evaporator to yield tetrabutylammonium-4-diphenylphoshino-butylsulfonate.

The following compounds can be synthesized accordingly:
1-Butyl-3-methyl-imidazolium 4-diphenylphoshino-butylsulfonate,
N-Butyl-pyridinium 4-diphenylphoshino-butylsulfonate,
N-Ethyl-pyridinium 4-diphenylphoshino-butylsulfonate,
N-Methyl-N-butyl-pyrrolidinium 4-diphenylphoshino-butylsulfonate,
N-Methyl-N-ethyl-pyrrolidinium 4-diphenylphoshino-butylsulfonate.

EXAMPLE 13

Synthesis of Tetrabutylammonium-5-carboxypentylsulfonate

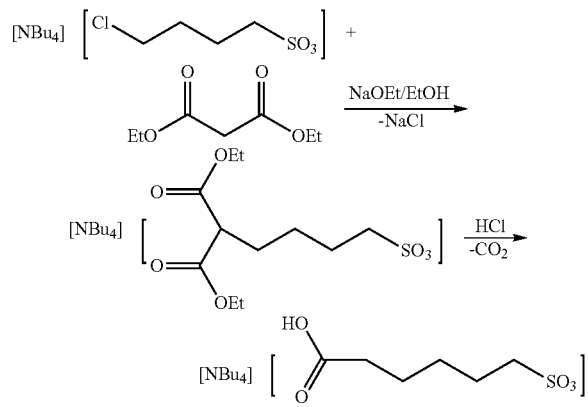

To a solution of tetrabutylammonium-4-chlorobutylsulfonate and malonic acid diethyl ester in ethanol a solution of NaOEt in ethanol is added dropwise under cooling. After complete addition, the solution is allowed to warm to room temperature. The precipitate is filtered off and the remaining solution is concentrated with a rotary evaporator to yield the ester adduct. This is refluxed in concentrated aqueous HCl. Removal of excess HCl with a rotary evaporator yields tetrabutylammonium-5-carboxypentylsulfonate.

LIST OF THE FIGURES

FIG. 1 describes results of detailed kinetic investigations of the synthesis of 1-butyl-3-methylimidazolium [BMIM] 4-chlorobutylsulfonate at different temperatures with the ratio [BMIM]Cl:1,4-butane sultone being 1:20 in the solvent nitroethane.

FIG. 2 describes AR-XP spectra of 3a ([BMIM] [ClC$_4$H$_8$SO$_3$]) in the C1s, N1s, O1s, S2p, and Cl2p regions. The spectra were collected at emission angles of 0° (black, bulk sensitive) and 70° (surface sensitive). In the Cl region, a chloride spectrum of [EMIM]Cl (right spectrum) is added for comparison. [EMIM] means ethyl-methyl-imidazolium.

The invention claimed is:
1. A compound of formula III

$$Kt^+[Y(CHR^a)_n—CH(R^a)SO_3]^- \quad\quad III$$

wherein
$R^a$ is H, or $C_{1-12}$-alkyl;
$R^b$ is $C_{1-12}$-alkyl;
n is 3;
$Kt^+$ is a non-metallic cation or $K^+$, $Na^+$, $Rb^+$, or $Cs^+$;
Y is F, Cl, Br, $R^b$—C(O)O or Nu;
Nu is $OR^o$, $OAr$, $SR^o$, $SAr$, $NHR^o$, $N(R^o)_2$, $CH(COOR^o)_2$, $P(R^o)_2$, $P(Ar)_2$, or $P(O)(OR^o)_2$;
$R^o$ is $C_{1-12}$-alkyl; and
Ar is an unsubstituted or substituted aromatic ring.

2. A compound according to claim 1, wherein the cation $Kt^+$ is an ammonium cation of formula (1)

$$[NR_4]^+ \quad\quad (1)$$

wherein
R in each case, independently of one another, denotes
H, with the proviso that at least two substitutes R in the formula (1) are H,
OR', NR'$_2$, with the proviso that at most one substituent R in the formula (1) is OR' or NR'$_2$,
straight-chain or branched alkyl having 1-20 C atoms,
straight-chain or branched alkenyl having 1-20 C atoms and one or more double bonds,
straight-chain or branched alkynyl having 2-20 C atoms and one or more triple bonds, saturated, partially or fully unsaturated cycloalkyl having 3-7 C atoms, which is optionally substituted by one or more alkyl groups having 1-6C atoms,
where one or more R are optionally partially or fully substituted by halogens, or partially by —OH, —OR', —CN, —C(O)OH, —C(O)NR'$_2$, —SO$_2$NR'$_2$, —C(O)X', —SO$_2$OH, —SO$_2$X' or —NO$_2$, and where one or two non-adjacent carbon atoms of the R which are not in the α-position are optionally replaced by atoms and/or atom groups selected from the group consisting of —O—, —S—, —S(O)—, —SO$_2$—, —SO$_2$O—, —C(O)—, —C(O)O—, —N$^+$R'$_2$, —P(O)R'O—, —C(O)NR'—, —SO$_2$NR'—, —OP(O)R'O—, —P(O)(NR'$_2$)NR'—, —PR'$_2$=N— and —P(=)R'—, where R' is H, a non-, partially or perfluorinated $C_{1-6}$-alkyl, $C_{3-7}$-cycloalkyl, or unsubstituted or substituted phenyl, and X' is halogen.

3. A compound according to claim 1, wherein the cation $Kt^+$ is a phosphonium cation of formula (2)

$$[PR^2_4]^+ \quad\quad (2),$$

wherein
$R^2$ in each case, independently of one another, denotes
H, OR', NR'$_2$, straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which is optionally substituted by one or more alkyl groups having 1-6 C atoms, where one or more $R^2$ are optionally partially or fully substituted by halogens, or partially by —OH, —OR', —CN, —C(O)OH, —C(O)NR'$_2$, —SO$_2$NR'$_2$, —C(O)X', —SO$_2$OH, —SO$_2$X' or —NO$_2$, and where one or two non-adjacent carbon atoms of the $R^2$ which are not in the α-position are optionally replaced by atoms and/or atom groups selected from the group consisting of —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— and —P(O)R'—, where R' is H, a non-, partially or perfluorinated C$_{1-6}$-alkyl, C$_{3-7}$-cycloalkyl, or unsubstituted or substituted phenyl, and X' is halogen.

4. A solvent or solvent additive, a phase-transfer catalyst, an extractant, a heat-transfer medium, a surface-active substance, a plasticizer, a flame retardant, an ionic liquid, a conductive salt, or an additive in electrochemical cells, comprising a compound according to claim 1.

5. A process for preparing a compound according to claim 1,
wherein Y is F, Cl, Br or $R^b$—C(O)O, comprising reacting a compound of formula Kt$^+$X$^-$ wherein X is F, Cl, Br, or $R^b$—C(O)O and Kt$^+$ is as defined for the compound of formula III,
with a compound of formula I

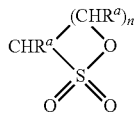

I wherein n, $R^a$, and $R^b$ are as defined for the compound of formula III,
or wherein Y is Nu, comprising substituting X in a nucleophilic substitution reaction with an alcoholate, phenolate, thiolate, thiophenolate, amide, malonate, phosphide, or phosphate.

6. A process according to claim 2, wherein the cation Kt$^+$ is an ammonium cation of formula (1)

[NR$_4$]$^+$ (1)

wherein
R in each case independently of one another, denotes
H, with the proviso that at least two substitutes R in the formula (1) are H,
OR', NR'$_2$, with the proviso that at most one substituent R in the formula (1) is OR' or NR'$_2$,
straight-chain or branched alkyl having 1-20 C atoms,
straight-chain or branched alkenyl having 1-20 C atoms and one or more double bonds,
straight-chain or branched alkynyl having 2-20 C atoms and one or more triple bonds,
saturated, partially or fully unsaturated cycloalkyl having 3-7 C atoms, which is optionally substituted by one or more alkyl groups having 1-6C atoms, where one or more R are optionally partially or fully substituted by halogens, or partially by —OH, —OR', —CN, —C(O)OH, —C(O)NR'$_2$, —SO$_2$NR'$_2$, —C(O)X', —SO$_2$OH, —SO$_2$X' or —NO$_2$and where one or two non-adjacent carbon atoms of the R which are not in the α-position are optionally replaced by atoms and/or atom groups selected from the group consisting of —O—, —S—, —S(O)—, —SO$_2$—, —SO$_2$O—, —C(O)—, —C(O)O—, —N$^+$R'$_2$—P(O)R'O—, —C(O)NR'—, —SO$_2$NR'—, —OP(O)R'O—, —P(O)(NR'$_2$)NR'—, —PR'$_2$=N— and —(=)R'—, where R' is H, a non-, partially or perfluorinated C$_{1-6}$-alkyl, C$_{3-7}$-cycloalkyl, or unsubstituted or substituted phenyl, and X' is halogen.

7. A process according to claim 2, wherein the cation Kt$^+$ is a phosphonium cation of formula (2)

[PR$^2_4$]$^+$ (2), wherein
$R^2$ in each case, independently of one another, denotes
H, OR', NR'$_2$,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which is optionally substituted by one or more alkyl groups having 1-6 C atoms, where one or more $R^2$ are optionally partially or fully substituted by halogens, or partially by —OH, —OR', —CN, —C(O)OH, —C(O)NR'$_2$, —SO$_2$NR'$_2$, —C(O)X', —SO$_2$OH, —SO$_2$X' or —NO$_2$, and where one or two non-adjacent carbon atoms of the $R^2$ which are not in the α-position are optionally replaced by atoms and/or atom groups selected from the group consisting of —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— and —P(O)R'—, where R' is H, a non-, partially or perfluorinated C$_{1-6}$-alkyl, C$_{3-7}$-cycloalkyl, or unsubstituted or substituted phenyl, and X' is halogen.

8. A process according to claim 2, wherein the cation Kt$^+$ is a uronium cation of formula (3)

[C(R$^3$R$^4$N)(OR$^5$)(NR$^6$R$^7$)]$^+$ (3), wherein
$R^3$ to $R^7$ each, independently of one another, denote
hydrogen, where hydrogen is excluded for $R^5$,
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which is optionally substituted by one or more alkyl groups having 1-6 C atoms, where one or more of the substituents $R^3$ to $R^7$ are optionally partially or fully substituted by halogens, or partially by —OH, —OR', —CN, —C(O)OH, —C(O)NR'$_2$—SO$_2$NR'$_2$—C(O)X', —SO$_2$OH, —SO$_2$X' or —NO$_2$and where one or two non-adjacent carbon atoms of $R^3$ to $R^7$ which are not in the α-position are optionally replaced by atoms and/or atom groups selected from the group consisting of —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— and —P(O)R'—, where R' is H, a non-, partially or perfluorinated $C_{1-6}$-alkyl, $C_{3-7}$-cycloalkyl, or unsubstituted or substituted phenyl, and X' is halogen.

9. A process according to claim 2, wherein the cation $Kt^+$ is a thiouronium cation of formula (4)

$$[C(R^3R^4N)(SR^5)(NR^6R^7)]^+ \quad (4),$$

wherein
$R^3$ to $R^7$ each, independently of one another, denote hydrogen, where hydrogen is excluded for $R^5$,
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which is optionally substituted by one or more alkyl groups having 1-6 C atoms, where one or more of the substituents $R^3$ to $R^7$ are optionally partially or fully substituted by halogens, or partially by —OH, —OR', —CN, —C(O)OH, —C(O)NR'$_2$—SO$_2$NR'$_2$—C(O)X', —SO$_2$OH, —SO$_2$X' or —NO$_2$ and where one or two non-adjacent carbon atoms of $R^3$ to $R^7$ which are not in the α-position are optionally replaced by atoms and/or atom groups selected from the group consisting of —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— and —P(O)R'—, where R' is H, a non-, partially or perfluorinated $C_{1-6}$-alkyl, $C_{3-7}$-cycloalkyl, or unsubstituted or substituted phenyl, and X' is halogen.

10. A process according to claim 2, wherein the cation $Kt^+$ is a guanidinium cation of formula (5)

$$[C(NR^8R^9)(NR^{10}R^{11})(NR^{12}R^{13})]^+ \quad (5),$$

wherein
$R^8$ to $R^{13}$ each, independently of one another, denote hydrogen, —CN, NR'$_2$—OR',
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which is optionally substituted by one or more alkyl groups having 1-6 C atoms, where one or more of the substituents $R^8$ to $R^{13}$ are optionally partially or fully substituted by halogens, or partially by —OH, —OR', —CN, —C(O)OH, —C(O)NR'$_2$, —SO$_2$NR'$_2$—C(O)X', —SO$_2$OH, —SO$_2$X' or —NO$_2$ and where one or two non-adjacent carbon atoms of $R^8$ to $R^{13}$ which are not in the α-position are optionally replaced by atoms and/or atom groups selected from the group consisting of —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— and —P(O)R'—, where R' is H, a non-, partially or perfluorinated $C_{11-6}$-alkyl, $C_{3-7}$-cycloalkyl, or unsubstituted or substituted phenyl, and X' is halogen.

11. A process according to claim 2, wherein the cation $Kt^+$ is of formula (6)

$$[HetN]^+ \quad (6)$$

wherein
HetN$^+$ denotes

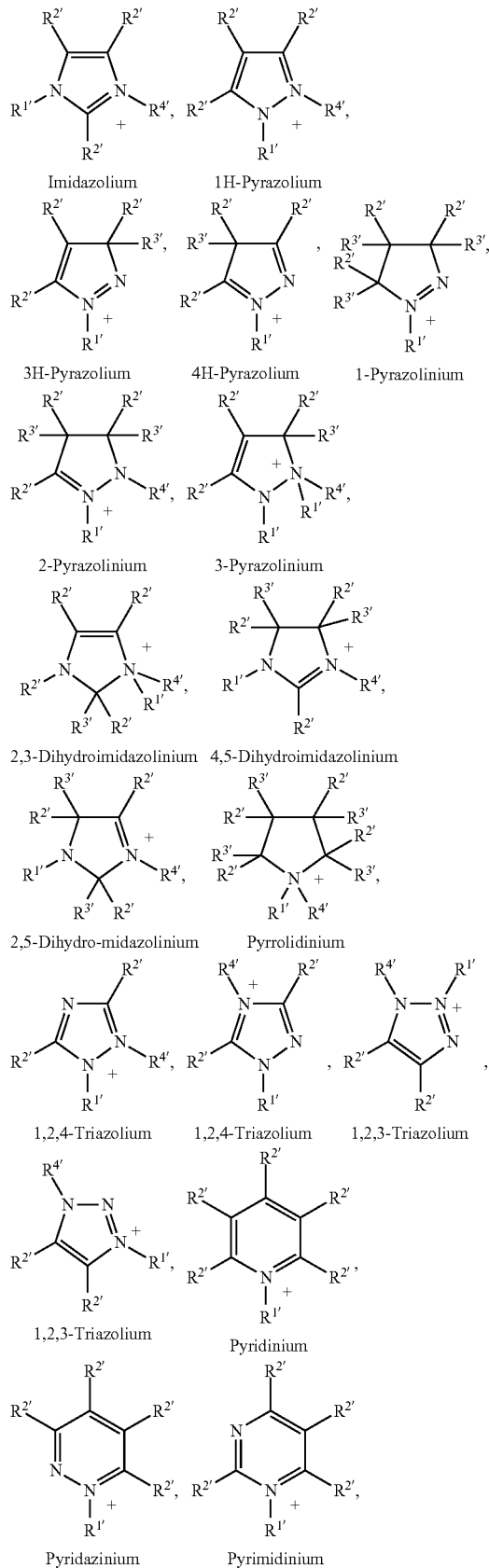

-continued

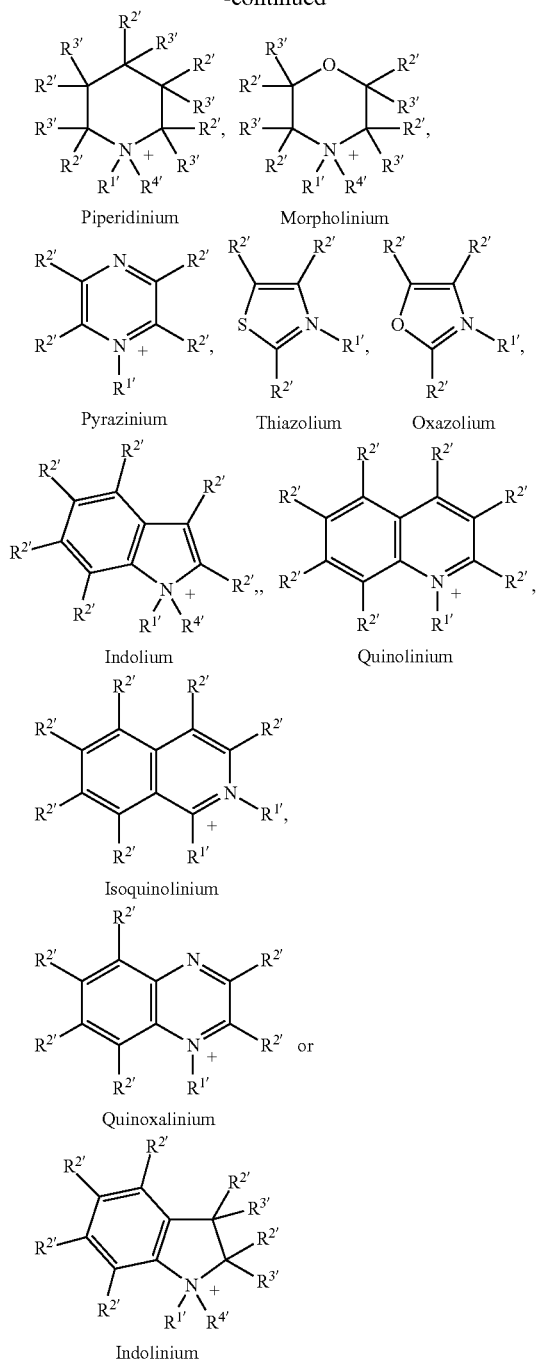

wherein
R¹' to R⁴' each, independently of one another, denote hydrogen, —CN, —OR', —NR'₂, —P(O)R'₂, —P(O)(OR')₂, —P(O)(NR'₂)₂—C(O)R', —C(O)OR',
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds, saturated, partially or fully unsaturated cycloalkyl having 3-7 C atoms, which is optionally substituted by one or more alkyl groups having 1-6 C atoms, saturated, partially or fully unsaturated heteroaryl, heteroaryl-$C_1$-$C_6$-alkyl or aryl-$C_1$-$C_6$-alkyl, or R¹', R²', R³' and/or R⁴' together may also form a ring system, where one or more of the substituents R¹' to R⁴' are optionally partially or fully substituted by halogens, or —OH, —OR', —CN, —C(O)OH, —C(O)NR'₂, —SO₂NR'₂, —C(O)X', —SO₂OH, —SO₂X' or —NO₂, but where R¹' and R⁴' cannot simultaneously be fully substituted by halogens, and where one or two non-adjacent carbon atoms of the substituents R¹' to R⁴' which are not bonded to the heteroatom are optionally replaced by atoms and/or atom groups selected from the group consisting of —O—, —S—, —S(O)—, —SO₂—, —SO₂O—, —C(O)—, —C(O)O—, —N⁺R'₂—P(O)R'O—, —C(O)NR'—, —SO₂NR'—, —OP(O)R'O—, —P(O)(NR'₂)NR'—, —PR'₂=N— and —P(O)R'—, where R' is H, a non-, partially or perfluorinated $C_{1-6}$-alkyl, $C_{3-7}$-cycloalkyl, or unsubstituted or substituted phenyl, and X' is halogen.

12. A solvent or solvent additive, a phase-transfer catalyst, an extractant, a heat-transfer medium, a surface-active substance, a plasticizer, a flame retardant, an ionic liquid, a conductive salt, or an additive in electrochemical cells, comprising a compound produced according to the process of claim 2.

13. A compound of formula III $$Kt^+[Y(CHR^a)_n—CH(R^a)SO_3]$$      III wherein
$R^a$ is H, or $C_{1-12}$-alkyl;
$R^b$ is $C_{1-12}$-alkyl;
n is 1 to 3;
Y is F, Cl, Br, $R^b$—C(O)O or Nu;
Nu is $OR^oAr$, $SR^o$, SAr, $NHR^o$, $N(R^o)_2$, $CH(COOR^o)_2$, $P(R^o)_2$, $P(Ar)_2$ or $P(O)(OR^o)_2$;
$R^o$ is $C_{1-12}$-alkyl;
Ar is an unsubstituted or substituted aromatic ring, and
$Kt^+$ is a uronium cation of formula (3)

$$[C(R^3R^4N)(OR^5)(NR^6R^7)]^+$$      (3), wherein
$R^3$ to $R^7$ each, independently of one another, denote
hydrogen, where hydrogen is excluded for $R^5$,
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which is optionally substituted by one or more alkyl groups having 1-6 C atoms, where one or more of the substituents $R^3$ to $R^7$ are optionally partially or fully substituted by halogens, or partially by —OH, —OR', —CN, —C(O)OH, —C(O)NR'₂, —SO₂NR'₂, —C(O)X', —SO₂OH, —SO₂X' or —NO₂ and where one or two non-adjacent carbon atoms of $R^3$ to $R^7$ which are not in the α-position are optionally replaced by atoms and/or atom groups selected from the group consisting of —O—, —S—, —S(O)—, —SO₂—, —SO₂O—, —C(O)—, —C(O)O—, —N⁺R'₂—, —P(O)R'O—, —C(O)NR'—, —SO₂R'—, —OP(O)R'O—, —P(O)(NR'₂)NR'—, —PR'₂=N— and —P(O)R'—, where R' is H, a non-, partially or perfluorinated $C_{1-6}$-alkyl, $C_{3-7}$-cycloalkyl, or unsubstituted or substituted phenyl, and X' is halogen;
or
$Kt^+$ is a thiouronium cation of formula (4)

$$[C(R^3R^4N)(SR^5)(NR^6R^7)]^+$$      (4), wherein
$R^3$ to $R^7$ each, independently of one another, denote
hydrogen, where hydrogen is excluded for $R^5$,
straight-chain or branched alkyl having 1 to 20 C atoms, straight-chain or branched alkenyl having 2-20 C atoms and one or more double bonds, straight-chain or branched alkynyl having 2-20 C atoms and one or more triple bonds, saturated, partially or fully unsaturated cycloalkyl having 3-7 C atoms, which is optionally substituted by one or more alkyl groups having 1-6 C atoms, where one or more of the substituents $R^3$ to $R^7$ are optionally partially or fully substituted by halogens, or partially by —OH, —OR', —CN, —C(O)OH, —C(O)NR'$_2$, —SO$_2$NR'$_2$, —C(O)X', —SO$_2$OH, —SO$_2$X' or —NO$_2$ and where one or two non-adjacent carbon atoms of $R^3$ to $R^7$ which are not in the α-position are optionally replaced by atoms and/or atom groups selected from the group consisting of —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$R'—, —OP(O)R'O—, —P(O)(NR'$_2$)NR'—, —PR'$_2$=N— and —P(O)R'—, where R' is H, a non-, partially or perfluorinated C$_{1-6}$-alkyl, C$_{3-7}$-cycloalkyl, or unsubstituted or substituted phenyl, and X' is halogen;

or

Kt$^+$ is a guanidinium cation of formula (5)

[C(NR$^8$R$^9$)(NR$^{10}$R$^{11}$)(NR$^{12}$R$^{13}$)]$^+$ (5), wherein $R^8$ to $R^{13}$ each, independently of one another, denote hydrogen, —CN, NR'$_2$, —OR', straight-chain or branched alkyl having 1 to 20 C atoms, straight-chain or branched alkenyl having 2-20 C atoms and one or more double bonds, straight-chain or branched alkynyl having 2-20 C atoms and one or more triple bonds, saturated, partially or fully unsaturated cycloalkyl having 3-7 C atoms, which is optionally substituted by one or more alkyl groups having 1-6 C atoms, where one or more of the substituents $R^8$ to $R^{13}$ are optionally partially or fully substituted by halogens, or partially by —OH, —OR', —CN, —C(O)OH, —C(O)NR'$_2$, —SO$_2$NR'$_2$, —C(O)X', —SO$_2$OH, —SO$_2$X' or —NO$_2$ and where one or two non-adjacent carbon atoms of $R^8$ to $R^{13}$ which are not in the α-position are optionally replaced by atoms and/or atom groups selected from the group consisting of —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— and —P(O)R'—, where R' is H, a non-, partially or perfluorinated C$_{1-6}$-alkyl, C$_{3-7}$-cycloalkyl, or unsubstituted or substituted phenyl, and X' is halogen;

or

Kt$^+$ is of formula (6)

[HetN]$^+$ (6)

wherein
HetN$^+$ denotes

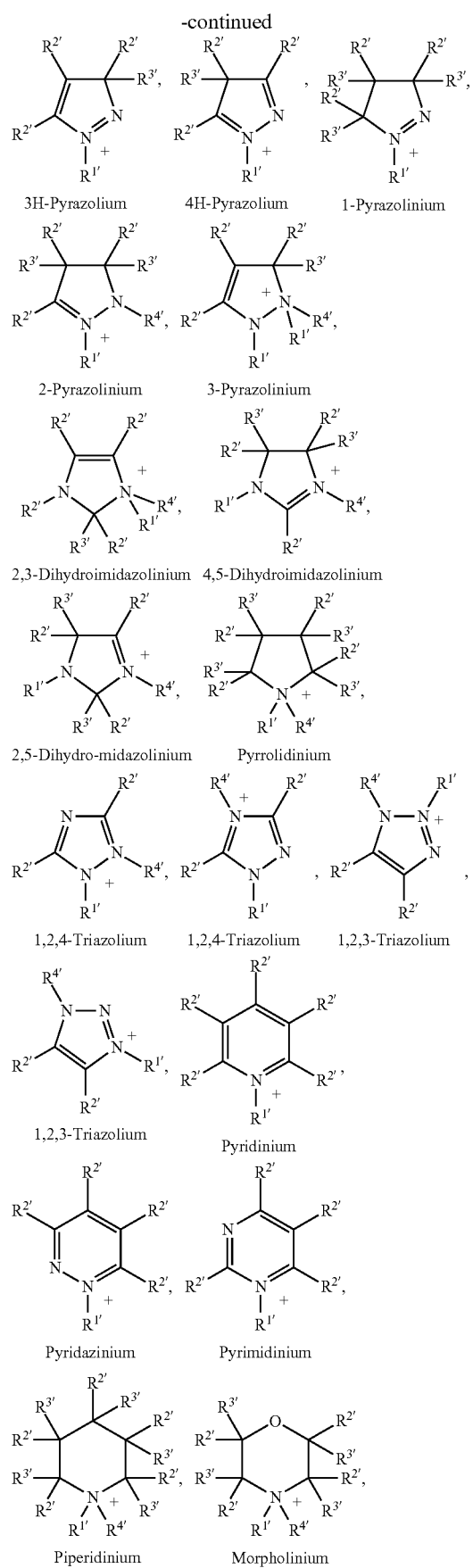

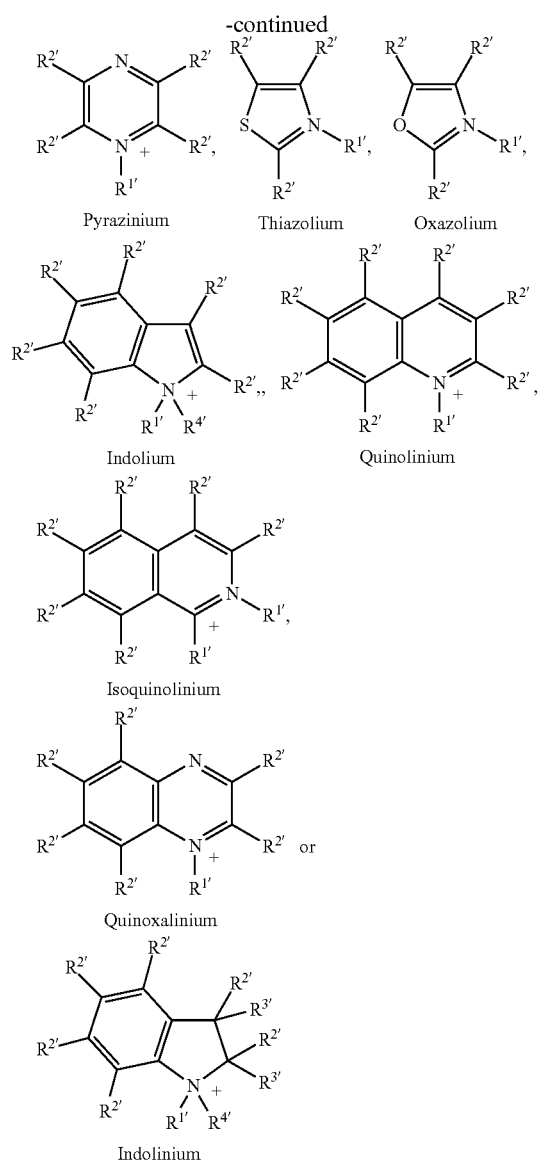

Pyrazinium  Thiazolium  Oxazolium

Indolium  Quinolinium

Isoquinolinium

Quinoxalinium

Indolinium wherein
$R^{1'}$ to $R^{4'}$ each, independently of one another, denote hydrogen, —CN, —OR', —NR'$_2$, —P(O)R'$_2$, —P(O)(OR')$_2$—P(O)(NR'$_2$)$_2$, —C(O)R', —C(O)OR',
straight-chain or branched alkyl having 1-20 C atoms,
straight-chain or branched alkenyl having 2-20 C atoms and one or more double bonds, straight-chain or branched alkynyl having 2-20 C atoms and one or more triple bonds,
saturated, partially or fully unsaturated cycloalkyl having 3-7 C atoms, which is optionally substituted by one or more alkyl groups having 1-6 C atoms, saturated, partially or fully unsaturated heteroaryl, heteroaryl-$C_1$-$C_6$-alkyl or aryl-C-$C_6$-alkyl,
or $R^{1'}$, $R^{2'}$, $R^{3'}$ and/or $R^{4'}$ together may form a ring system, where one or more of the substituents $R^{1'}$ to $R^{4'}$ are optionally partially or fully substituted by halogens, or —OH, —OR', —CN, —C(O)OH, —C(O)NR'$_2$, —SO$_2$NR'$_2$, —C(O)X', —SO$_2$OH, —SO$_2$X' or —NO$_2$ but where $R^{1'}$ and $R^{4'}$ cannot simultaneously be fully substituted by halogens, and where one or two non-adjacent carbon atoms of the substituents $R^{1'}$ to $R^{4'}$ which are not bonded to the heteroatom are optionally replaced by atoms and/or atom groups selected from the group consisting of —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— and —P(O)R'—, where R' is H, a non-, partially or perfluorinated $C_{1-6}$-alkyl, $C_{3-7}$-cycloalkyl, or unsubstituted or substituted phenyl, and X' is halogen.

14. A compound according to claim 7, wherein n is 3.

15. A compound according to claim 7, wherein the cation Kt$^+$ is a uronium cation of formula (3)

$$[C(R^3R^4N)(OR^5)(NR^6R^7)]^+ \quad (3),$$

wherein
$R^3$ to $R^7$ each, independently of one another, denote hydrogen, where hydrogen is excluded for $R^5$,
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which is optionally substituted by one or more alkyl groups having 1-6 C atoms, where one or more of the substituents $R^3$ to $R^7$ are optionally partially or fully substituted by halogens, or partially by —OH, —OR', —CN, —C(O)OH, —C(O)NR'$_2$, —SO$_2$NR'$_2$, —C(O)X', —SO$_2$OH, —SO$_2$X' or —NO$_2$, and where one or two non-adjacent carbon atoms of $R^3$ to $R^7$ which are not in the α-position are optionally replaced by atoms and/or atom groups selected from the group consisting of —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— and —P(O)R'—, where R' is H, a non-, partially or perfluorinated $C_{1-6}$-alkyl, $C_{3-7}$-cycloalkyl, or unsubstituted or substituted phenyl, and X' is halogen.

16. A compound according to claim 7, wherein the cation Kt$^+$ is a thiouronium cation of formula (4)

$$[C(R^3R^4N)(SR^5)(NR^6R^7)]^+ \quad (4),$$

wherein
$R^3$ to $R^7$ each, independently of one another, denote hydrogen, where hydrogen is excluded for $R^5$,
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which is optionally substituted by one or more alkyl groups having 1-6 C atoms, where one or more of the substituents $R^3$ to $R^7$ are optionally partially or fully substituted by halogens, or partially by —OH, —OR', —CN, —C(O)OH, —C(O)NR'$_2$, —SO$_2$NR'$_2$, —C(O)X', —SO$_2$OH, —SO$_2$X' or —NO$_2$ and where one or two non-adjacent carbon atoms of $R^3$ to $R^7$ which are not in the α-position are optionally replaced by atoms and/or atom groups selected from the group consisting of —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— and —P(O)R'—, where R' is H, a non-, partially or perfluorinated $C_{1-6}$-alkyl, $C_{3-7}$-cycloalkyl, or unsubstituted or substituted phenyl, and X' is halogen.

17. A compound according to claim 7, wherein the cation $Kt^+$ is a guanidinium cation of formula (5)

[C(NR$^8$R$^9$)(NR$^{10}$R$^{11}$)(NR$^{12}$R$^{13}$)]$^+$ (5), wherein $R^8$ to $R^{13}$ each, independently of one another, denote hydrogen, —CN, NR'$_2$—OR', straight-chain or branched alkyl having 1to 20 C atoms, straight-chain or branched alkenyl having 2-20 C atoms and one or more double bonds, straight-chain or branched alkynyl having 2-20 C atoms and one or more triple bonds, saturated, partially or fully unsaturated cycloalkyl having 3-7 C atoms, which is optionally substituted by one or more alkyl groups having 1-6 C atoms, where one or more of the substituents $R^8$ to $R^{13}$ are optionally partially or fully substituted by halogens, or partially by —OH, —OR', —CN, —C(O)OH, —C(O)NR'$_2$, —SO$_2$NR'$_2$, —C(O)X', —SO$_2$OH, —SO$_2$X' or —NO$_2$ and where one or two non-adjacent carbon atoms of $R^8$ to $R^{13}$ which are not in the α-position are optionally replaced by atoms and/or atom groups selected from the group consisting of —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— and —P(O)R'—, where R' is H, a non-, partially or perfluorinated $C_{11-6}$-alkyl, $C_{3-7}$-cycloalkyl, or unsubstituted or substituted phenyl, and X' is halogen.

18. A compound according to claim 7, wherein the cation $Kt^+$ is of the formula (6)

[HetN]$^+$ (6)

wherein

HetN$^+$ denotes

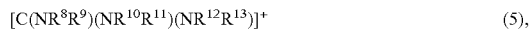

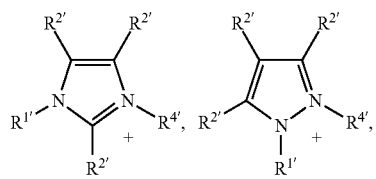

Imidazolium    1H-Pyrazolium

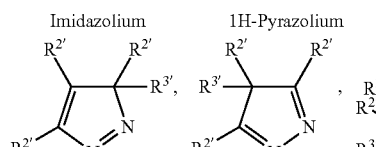

3H-Pyrazolium    4H-Pyrazolium    1-Pyrazolinium

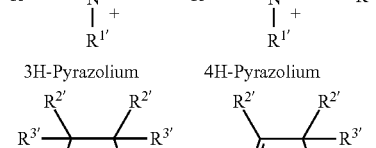

2-Pyrazolinium    3-Pyrazolinium

2,3-Dihydroimidazolinium    4,5-Dihydroimidazolinium

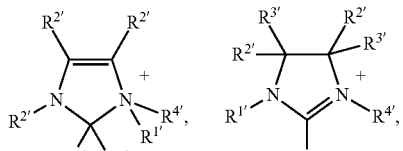

2,5-Dihydro-midazolinium    Pyrrolidinium

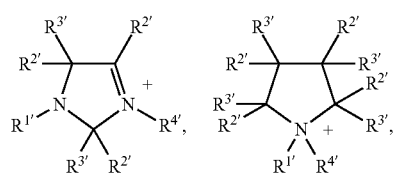

1,2,4-Triazolium    1,2,4-Triazolium    1,2,3-Triazolium

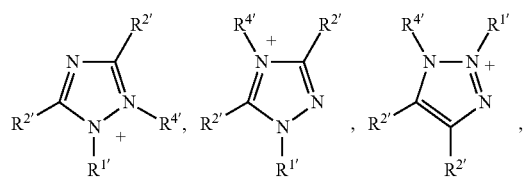

1,2,3-Triazolium    Pyridinium

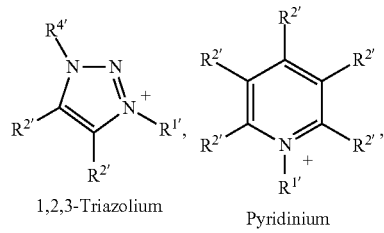

Pyridazinium    Pyrimidinium

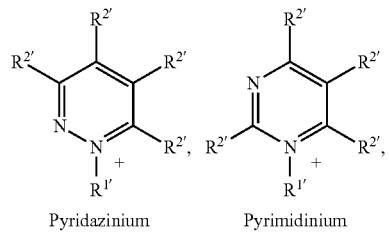

Piperidinium    Morpholinium

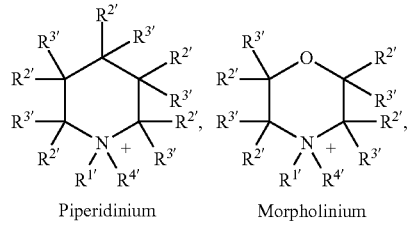

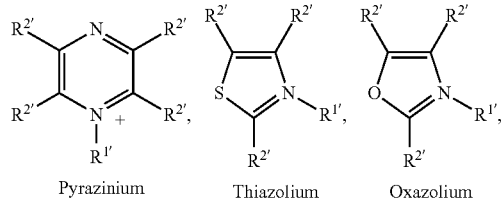

Pyrazinium    Thiazolium    Oxazolium

-continued

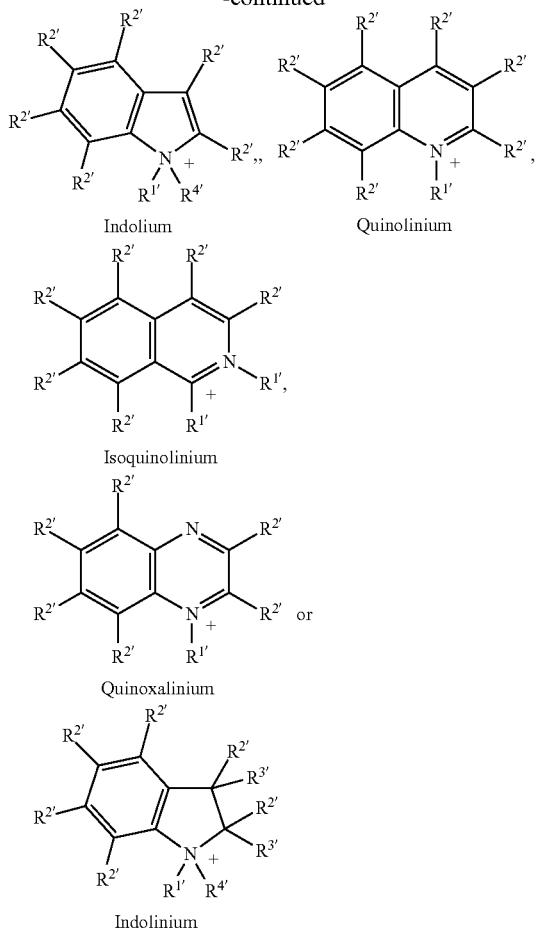

Indolium

Quinolinium

Isoquinolinium

Quinoxalinium

Indolinium wherein
R$^{1'}$ to R$^{4'}$ each, independently of one another, denote
hydrogen, —CN, —OR', —NR'$_2$—P(O)R'$_2$, —P(O)(OR')$_2$, —P(O)(NR'$_2$)$_2$, —C(O)R', —C(O)OR',
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which is optionally substituted by one or more alkyl groups having 1-6 C atoms, saturated, partially or fully unsaturated heteroaryl, heteroaryl-C$_1$-C$_6$-alkyl or aryl-C$_1$-C$_6$-alkyl, or R$^{1'}$, R$^{2'}$, R$^{3'}$and/or R$^{4'}$together may form a ring system, where one or more of the substituents R$^{1'}$ to R$^{4'}$ are optionally partially or fully substituted by halogens, or —OH, —OR', —CN, —C(O)OH, —C(O)NR'$_2$, —SO$_2$NR'$_2$, —C(O)X', —SO$_2$OH, —SO$_2$X' or —NO$_2$, but where R$^{1'}$ and R$^{4'}$ cannot simultaneously be fully substituted by halogens, and where one or two non-adjacent carbon atoms of the substituents R$^{1'}$ to R$^{4'}$ which are not bonded to the heteroatom are optionally replaced by atoms and/or atom groups selected from the group consisting of —O—, —S—, —S(O)—, —SO$_2$—, —SO$_2$O—, —C(O)—, —C(O)O—, —N$^+$R'$_2$, —P(O)R'O—, —C(O)NR'—, —SO$_2$NR'—, —OP(O)R'O—, —P(O)(NR'$_2$)NR'—, —PR'$_2$=N— and —P(O)R'—, where R' is H, a non-, partially or perfluorinated C$_{1-6}$-alkyl, C$_{3-7}$-cycloalkyl, or unsubstituted or substituted phenyl, and X' is halogen.

19. A process for preparing a compound according to claim 7, wherein Y is F, Cl, Br or R$^b$—C(O)O, comprising reacting a compound of formula Kt$^+$X$^-$ wherein X is F, Cl, Br, or R$^b$—C(O)O and Kt$^+$ is as defined for the compound of formula III,
with a compound of formula I

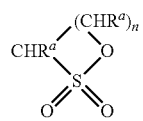

I wherein n, R$^a$, and R$^b$ are as defined for the compound of formula III,
or wherein Y is Nu, comprising substituting X in a nucleophilic substitution reaction with an alcoholate, phenolate, thiolate, thiophenolate, amide, malonate, phosphide, or phosphate.

* * * * *

UNITED STATES PATENT AND TRADEMARK OFFICE
CERTIFICATE OF CORRECTION

| | | |
|---|---|---|
| PATENT NO. | : 8,642,778 B2 | Page 1 of 1 |
| APPLICATION NO. | : 12/994323 | |
| DATED | : February 4, 2014 | |
| INVENTOR(S) | : Peter Wasserscheid et al. | |

It is certified that error appears in the above-identified patent and that said Letters Patent is hereby corrected as shown below:

In the Claims:

Column 28, Line 11 reads: "-PR'$_2$=N- and –(=)R'-, where R' is H, a non-," should read -- PR'$_2$=N- and –P(=)R'-, where R' is H, a non-, --.

Column 29, Line 61 reads: "is H, a non-, partially or perfluorinated $C_{11-6}$-alkyl, $C_{3-7}$-" should read -- is H, a non-, partially or perfluorinated $C_{1-6}$-alkyl, $C_{3-7}$- --.

Column 33, Line 11 reads: "-C(O)X', -SO$_2$OH, -SO$_2$X' or -NO$_2$and where" should read -- -C(O)X', -SO$_2$OH, -SO$_2$X' or –NO$_2$ and where --.

Column 33, Line 41 reads: "-C(O)X', -SO$_2$OH, -SO$_2$X' or -NO$_2$and where one" should read -- "-C(O)X', -SO$_2$OH, -SO$_2$X' or –NO$_2$ and where one --.

Signed and Sealed this
Twenty-seventh Day of May, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,642,778 B2  Page 1 of 1
APPLICATION NO. : 12/994323
DATED : February 4, 2014
INVENTOR(S) : Wasserscheid et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 456 days.

Signed and Sealed this
Twenty-ninth Day of September, 2015

Michelle K. Lee
*Director of the United States Patent and Trademark Office*